US 7,045,589 B2

(12) United States Patent
Heller et al.

(10) Patent No.: US 7,045,589 B2
(45) Date of Patent: May 16, 2006

(54) BIOERODIBLE POLY(ORTHO ESTERS) FROM DIOXANE-BASED DI(KETENE ACETALS), AND BLOCK COPOLYMERS CONTAINING THEM

(75) Inventors: Jorge Heller, Woodside, CA (US); Steven Y. Ng, San Francisco, CA (US)

(73) Assignee: A.P. Pharma, Inc., Redwood City, CA (US)

( * ) Notice: Subject to any disclaimer, the term of this patent is extended or adjusted under 35 U.S.C. 154(b) by 540 days.

(21) Appl. No.: 10/298,151

(22) Filed: Nov. 15, 2002

(65) Prior Publication Data

US 2004/0096506 A1   May 20, 2004

(51) Int. Cl.
*C08G 59/00* (2006.01)
*C08G 65/00* (2006.01)
*C08G 67/02* (2006.01)

(52) U.S. Cl. .................. 528/403; 528/392; 656/53; 424/478.08; 424/486; 424/443; 424/450; 424/468; 525/63

(58) Field of Classification Search ............... 424/486, 424/478.08, 443, 450, 468; 514/772.3; 528/403, 528/392; 606/53; 525/63
See application file for complete search history.

(56) References Cited

U.S. PATENT DOCUMENTS

| | | | |
|---|---|---|---|
| 3,268,550 A | 8/1966 | Heller | 260/315 |
| 4,014,987 A | 3/1977 | Heller et al. | 424/432 |
| 4,079,038 A | 3/1978 | Choi et al. | 260/47 XA |
| 4,093,709 A | 6/1978 | Choi et al. | 424/19 |
| 4,131,648 A | 12/1978 | Choi et al. | 424/22 |
| 4,131,662 A | 12/1978 | Cekoric et al. | 264/51 |
| 4,138,344 A | 2/1979 | Choi et al. | 252/1 |
| 4,180,064 A | 12/1979 | Heller et al. | 128/833 |
| 4,180,646 A | 12/1979 | Choi et al. | 528/153 |
| 4,249,531 A | 2/1981 | Heller et al. | 424/426 |
| 4,261,969 A | 4/1981 | Heller | 424/433 |
| 4,304,767 A | 12/1981 | Heller et al. | 424/78 |
| 4,502,976 A | 3/1985 | Heller | 516/108 |
| 4,513,143 A | 4/1985 | Ng et al. | 549/335 |
| 4,532,335 A | 7/1985 | Helwing | 549/335 |
| 4,549,010 A | 10/1985 | Sparer et al. | 528/361 |
| 4,639,366 A | 1/1987 | Heller | 424/484 |
| 4,710,497 A | 12/1987 | Heller et al. | 514/221 |
| 4,713,441 A | 12/1987 | Heller et al. | 528/392 |
| 4,745,160 A | 5/1988 | Churchill et al. | 525/419 |
| 4,764,364 A | 8/1988 | Heller et al. | 424/78 |
| 4,765,973 A | 8/1988 | Heller | 424/486 |
| 4,801,457 A | 1/1989 | Heller et al. | 424/422 |
| 4,855,132 A | 8/1989 | Heller et al. | 424/78 |
| 4,898,928 A | 2/1990 | Heller et al. | 528/392 |
| 4,946,931 A | 8/1990 | Heller et al. | 528/230 |
| 4,957,998 A | 9/1990 | Heller et al. | 528/220 |
| 5,030,457 A | 7/1991 | Ng et al. | 424/486 |
| 5,133,739 A | 7/1992 | Bezwada et al. | 606/230 |
| 5,336,505 A | 8/1994 | Ng et al. | 424/486 |
| 5,412,072 A | 5/1995 | Sakurai et al. | 530/322 |
| 5,449,513 A | 9/1995 | Yokoyama et al. | 424/78.08 |
| 5,461,140 A | 10/1995 | Heller et al. | 528/425 |
| 5,510,103 A | 4/1996 | Yokoyama et al. | 424/78.08 |
| 5,518,730 A | 5/1996 | Fuisz | 424/426 |
| 5,540,912 A | 7/1996 | Roorda et al. | 424/422 |
| 5,607,686 A | 3/1997 | Totakura et al. | 424/426 |
| 5,620,697 A | 4/1997 | Törmälä et al. | 424/426 |
| 5,626,862 A | 5/1997 | Brem et al. | 424/426 |
| 5,651,986 A | 7/1997 | Brem et al. | 424/484 |
| 5,693,751 A | 12/1997 | Sakurai et al. | 530/322 |
| 5,759,563 A | 6/1998 | Yewey et al. | 424/426 |
| 5,824,343 A | 10/1998 | Ng et al. | 424/486 |
| 5,939,453 A | 8/1999 | Heller et al. | 514/452 |
| 5,968,543 A | 10/1999 | Heller et al. | 424/425 |
| 5,993,856 A | 11/1999 | Ragavan et al. | 424/489 |
| 6,007,845 A | 12/1999 | Domb et al. | 424/501 |
| 6,046,187 A | 4/2000 | Berde et al. | 514/180 |
| 6,143,314 A | 11/2000 | Chandrashekar et al. | 424/426 |
| 6,372,245 B1 | 4/2002 | Bowman et al. | 424/427 |
| 6,524,606 B1 | 2/2003 | Ng et al. | 424/425 |
| 6,590,059 B1 | 7/2003 | Ng et al. | 528/220 |
| 6,613,355 B1 | 9/2003 | Ng et al. | 424/462 |
| 2002/0037300 A1 | 3/2002 | Ng et al. | 424/401 |
| 2002/0082362 A1 | 6/2002 | Brocchini et al. | 525/461 |
| 2002/0168336 A1 | 11/2002 | Ng et al. | 424/78.38 |
| 2002/0176844 A1 | 11/2002 | Ng et al. | 424/78.38 |
| 2003/0130472 A1 | 7/2003 | Ng et al. | 528/73 |
| 2003/0138474 A1 | 7/2003 | Ng et al. | 424/425 |

(Continued)

FOREIGN PATENT DOCUMENTS

EP   0419156   3/1991

(Continued)

OTHER PUBLICATIONS

Beyerstedt et al., "The preparation and properties of ketene diethylacetal", *J. Amer. Chem. Soc.*, 58:529-531 (1936).
Crivello et al., "Ketene acetal monomers: synthesis and characterization", *J. Polym. Sci., Part A: Polym Chem.*, 34:3091-3102 (1996).
Duncan et al. "The role of polymer conjugates in the diagnosis and treatment of cancer", *STP Pharma Sci.*, 6:237-273 (1996).

(Continued)

*Primary Examiner*—Duc Truong
(74) *Attorney, Agent, or Firm*—Heller Ehrman LLP

(57) ABSTRACT

Bioerodible poly(ortho esters) useful as orthopedic implants or vehicles for the sustained delivery of pharmaceutical, cosmetic and agricultural agents from dioxane-based di(ketene acetals). Block copolymers contain these bioerodible poly(ortho esters). These block copolymers have both hydrophilic and hydrophobic blocks. They form micelles in aqueous solution, making them suitable for encapsulation or solubilization of hydrophobic or water-insoluble materials; and they also form bioerodible matrices for the sustained release of active agents.

11 Claims, No Drawings

U.S. PATENT DOCUMENTS

2003/0152630 A1    8/2003    Ng et al. ............... 424/486

FOREIGN PATENT DOCUMENTS

| EP | 0524831 | 1/1993 |
|----|---------|--------|
| EP | 1142596 | 10/2001 |
| WO | 9103510 | 3/1991 |
| WO | 9414417 | 7/1994 |
| WO | 9632419 | 10/1996 |
| WO | 9725980 | 7/1997 |
| WO | 9962983 | 12/1999 |
| WO | WO 01/85139 | 11/2001 |
| WO | 0185139 | 4/2002 |
| WO | WO 02/092661 A1 | 11/2002 |

OTHER PUBLICATIONS

Haworth et al., "*Cis*- and *trans*-tetramethylene-(1:3)-dicarboxylic acids and the condensation of formaldehyde with ethylic malonate", *J. Chem. Soc.*, 73:330-345 (1898).

Haydock et al., "3,3$^1$-Ethylenediglutarimide as a potential tumor inhibitor", *J. Med. Chem.*, 15:447-448 (1972).

Kwon et al., "Block copolymer micelles as long-circulating drug vehicles", *Adv. Drug. Del. Rev.*, 16:295-309 (1995).

Meincke et al., "The cyclization of certain ethylene dimalonic esters by sodium ethoxide", *J. Amer. Chem. Soc.*, 57:1133-1135 (1935).

Roberts, "The role of neighboring groups in replacement reactions . . . ", *J. Amer. Chem. Soc.*, 80:1247-1254 (1958).

Wolthuis et al., "Synthesis and characterization of poly(ethylene glycol) poly-L-lactide block copolymers", *Third Eur. Symp. Controlled Drug Del.*, 271-276 (1994).

Yolles et al., "Sustained delivery of drugs from polymer/drug mixtures", *Polymer News*, 1:9-15 (1970).

Youxin et al., "Synthesis and properties of biodegradable ABA triblock copolymers . . . ", *J. Controlled Rel.*, 27:247-257 (1993).

Heller et al. "Controlled drug release by polymer dissolution. II: Enzyme-mediated delivery device", *J Pharm Sci.*, 68(7):919-921 (1979).

Heller, J., "Controlled release of biologically active compounds from bioerodible polymers", *Biomaterials*, 1:51-57 (1980).

Heller et al, "Controlled release of contraceptive steroids from biodegradable poly (ortho esters)", *Contraceptive Delivery Systems*, 4(1):43-53 (1983).

Heller et al., "Controlled release of water-soluble macromolecules from bioerodible hyrogels",*Biomaterials*, 4(4):262-6 (1983).

Heller J., "Biodegradable polymers in controlled drug delivery",*Crit Rev Ther Drug Carrier Syst.*, 1(1):39-90 (1984).

Heller J., Controlled drug release from poly(ortho esters) *Ann N Y Acad Sci.*, 446:51-66 (1985).

Heller, J. and J.K. Himmelstein, "Poly(ortho ester) Biodegradable Polymer Systems", *Methods in Enzymology*, 112:422-436 (1985).

Heller et al., "Controlled drug release from bioerodible hydrophobic ointments", *Biomaterials*, 11(4):235-7 (1990).

Heller J., "Modulated release from drug delivery devices", *Crit Rev Ther Drug Carrier Syst*, 10(3):253-305 (1993).

Heller J., "The use of polymers in the construction of controlled-release devices", *NIDA Res Monogr*, 154:107-31 (1995).

Heller et al., "Poly(ortho esters)—their development and some recent applications", *Eur J Pharm Biopharm*,50(1):121-128 (2000). Erratum in: *Eur J Pharm Biopharm*, 50(2):327.

Heller et al., "Poly(ortho esters): synthesis, characterization,properties and uses", *Adv Drug Deliv Rev.*, 54(7):1015-39 (2002).

Heller et al., "Development and applications of injectable poly(ortho esters) for pain control and periodontal treatment", *Biomaterials*, 23(22):4397-4404 (2002).

Ng et al., "Controlled drug release from self-catalyzed poly(ortho esters)", *Ann N Y Acad. Sci.*, 831:168-178 (1997).

Ng et al., "Development of a poly(ortho ester) prototype with a latent acid in the plymer backbone for 5-fluoruracil delivery", *J Control Release*, 65:367-74 (2000).

BIOERODIBLE POLY(ORTHO ESTERS) FROM DIOXANE-BASED DI(KETENE ACETALS), AND BLOCK COPOLYMERS CONTAINING THEM

BACKGROUND OF THE INVENTION

1. Field of the Invention

This application relates to poly(ortho esters). In particular, this invention relates to bioerodible poly(ortho esters) from dioxane-based di(ketene acetals); and to block copolymers containing them.

2. Description of the Related Art

Interest in synthetic biodegradable polymers for the systemic delivery of therapeutic agents began in the early 1970's with the work of Yolles et al, *Polymer News* 1:9–15 (1970) using poly(lactic acid). Since that time, numerous other polymers have been prepared and investigated as bioerodible matrices for the controlled release of therapeutic agents.

U.S. Pat. Nos. 4,079,038, 4,093,709, 4,131,648, 4,138,344 and 4,180,646 disclose biodegradable or bioerodible poly(ortho esters). These polymers are formed by a reaction between an orthoester (or orthocarbonate) such as 2,2-diethoxytetrahydrofuran and a diol such as 1,4-cyclohexanedimethanol. The reaction requires elevated temperature and reduced pressure and a relatively long reaction time. Drugs or other active agents are retained in the polymer matrix to be released as the polymer biodegrades due to hydrolysis of the labile linkages.

U.S. Pat. No. 4,304,767 discloses polymers prepared by reacting a polyol with a polyfunctional ketene acetal. These polymers represent a significant improvement over those of U.S. Pat. Nos. 4,079,038, 4,093,709, 4,131,648, 4,138,344 and 4,180,646, since synthesis proceeds readily at room temperature and atmospheric pressure, and the resulting polymers have superior properties.

Further polymers are disclosed in U.S. Pat. No. 4,957,998. These polymers contain acetal, carboxy-acetal and carboxy-orthoester linkages, and are prepared by a two-step process beginning with the reaction between a polyfunctional ketene acetal and a compound containing a vinyl ether, followed by reaction with a polyol or polyacid.

Still further polymers of a similar type are disclosed in U.S. Pat. No. 4,946,931. The polymers are formed by a reaction between a compound containing a multiplicity of carboxylate functions and a polyfunctional ketene acetal. The resulting polymers have very rapid erosion times.

Despite the ease with which the orthoester linkage hydrolyses, poly(ortho esters) known in the prior art are extremely stable materials when placed in an aqueous buffer, or when residing in the body. This stability is attributable to the extreme hydrophobicity of the poly(ortho esters) which severely limits the amount of water that can penetrate the polymer. To achieve useful erosion rates, therefore, acidic excipients must be physically incorporated into the polymer. While this allows control over erosion rates, the physically incorporated acidic excipient can diffuse from the polymer matrix at varying rates, leaving a matrix that is completely depleted of excipient while the polymer still has a very long lifetime remaining.

U.S. Pat. Nos. 4,764,364 and 4,855,132 describe bioerodible polymers, in particular poly(ortho esters) containing an amine functionality. The polymers are said to erode more rapidly at lower pH than at higher pH in an acidic aqueous environment.

Micellar System for Tumor Targeting

One of the major problems in treating cancer is the difficulty of achieving a sufficient concentration of an anticancer agent in the tumor. This is due to the toxicity, sometimes extreme, of such agents which severely limits the amounts that can be used. However, a major discovery in cancer chemotherapy has been the so-called EPR (enhanced permeation and retention) effect. The EPR effect is based on the observation that tumor vasculature, being newly formed vasculature, has an incompletely formed epithelium and is much more permeable than established older vasculature which is essentially impermeable to large molecules. Further, lymphatic drainage in tumors is very poor thus facilitating retention of anticancer agents delivered to the tumor.

The EPR effect can be used in cancer targeting by using delivery systems containing anticancer drugs that are too large to permeate normal vasculature, but which are small enough to permeate tumor vasculature, and two approaches have been developed. In one approach, a water-soluble polymer is used that contains an anticancer drug chemically bound to the polymer via a hydrolytically labile linkage. Such drug-polymer constructs are injected intravenously and accumulate in the tumors, where they are internalized by the cells via endocytosis and released in the lysosomal compartment of the cell via enzymatic cleavage of the labile bond attaching the drug to the polymer. Two disadvantages of this approach are that, first, nondegradable, water-soluble polymers have been used, and this requires a tedious fractionation of the polymer to assure that the molecular weight of the polymer is below the renal excretion threshold, and, second, the drug must be chemically attached to the polymer, which in effect creates a new drug entity with consequent regulatory hurdles that must be overcome. The use of polymer conjugates in cancer diagnosis and treatment is discussed in Duncan et al., "The role of polymer conjugates in the diagnosis and treatment of cancer", *S. T. P. Pharma Sciences*, 6(4), 237–263 (1996), and an example of an alginate-bioactive agent conjugate is given in U.S. Pat. No. 5,622,718.

An alternate approach has been described. In this approach, an AB or ABA block copolymer is prepared where the B-block is hydrophobic and the A-block is hydrophilic. When such a material is placed in water, it will self-assemble into micelles with a hydrophobic core and a hydrophilic shell surrounding the core. Such micelles have a diameter of about 100 nm, which is large enough that when they are injected intravenously, the micelles can not leave the normal vasculature, but they are small enough to leave the vasculature within tumors. Further, a 100 nm diameter is too small to be recognized by the reticuloendothelial system, thus enhancing micelle lifetime within the blood stream. Additionally, when the hydrophilic block is poly(ethylene glycol), further enhancement of circulation time is noted, as has been observed with "stealth" liposomes. The use of block copolymer micelles is reviewed in Kwon et al., "Block copolymer micelles as long-circulating drug delivery vehicles", *Adv. Drug Delivery Rep.*, 16, 295–309 (1995).

U.S. Pat. Nos. 5,412,072; 5,449,513; 5,510,103; and 5,693,751 describe block copolymers useful as micellar delivery systems where the hydrophilic block is polyethylene glycol and the hydrophobic blocks are various derivatives of poly(aspartic acid), poly(glutamic acid) and polylysine. U.S. Pat. Nos. 5,412,072 and 5,693,751 describe an approach where drugs have been chemically attached to the hydrophobic segment; while U.S. Pat. Nos. 5,449,513 and 5,510,103 describe an approach where hydrophobic drugs have been physically entrapped within the hydrophobic portion of the micelle. This latter approach is clearly preferable because no chemical modification of the drug is necessary.

Bioerodible Block Copolymer Matrix for Controlled Drug Delivery

In AB, ABA, or BAB block copolymers comprising a hydrophilic A block and a hydrophobic B block, the A and B blocks are incompatible and on a microscopic scale will phase-separate. This phase separation imparts unique and useful thermal properties to the material.

There is considerable prior art in the development of block copolymers comprised of poly(ethylene glycol) and bioerodible hydrophobic segments such as poly(L-lactic acid), poly(L-lactic-co-glycolic acid) copolymers and poly (ε-caprolactone), and discussion of their use as drug delivery agents. For example, see Wolthuis et al., "Synthesis and characterization of poly(ethylene glycol) poly-L-lactide block copolymers", *Third Eur. Symp. Controlled Drug Delivery* 271–276 (1994), Youxin et al., "Synthesis and properties of biodegradable ABA triblock copolymers . . . ", *J. Controlled Release,* 27, 247–257 (1993), and U.S. Pat. No. 5,133,739.

Poly(ortho esters) are known as potential vehicles for sustained release drug delivery. See, for example, Heller, "Poly(Ortho Esters)", *Adv. Polymer Sci.,* 107, 41–92 (1993), and references cited therein, and U.S. Pat. Nos. 4,304,767, 4,946,931, 4,957,998, and 5,968,543.

U.S. Pat. No. 5,939,453 describes block copolymers prepared from polyethylene glycols and certain poly(ortho esters).

The documents listed in this section and elsewhere throughout this application are incorporated into this application by reference.

SUMMARY OF THE INVENTION

In a first aspect, this invention is poly(ortho esters) of formula I:

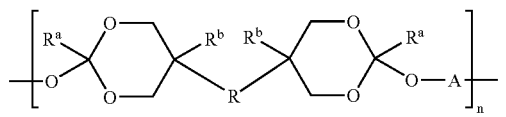

where
n is an integer of at least 5;
R is a bond, $-(CH_2)_a-$, or $-(CH_2)_b-O-(CH_2)_c-$; where a is an integer of 1 to 10, and b and c are independently integers of 1 to 5;
$R^a$ is a $C_1-C_4$ alkyl;
$R^b$ is hydrogen or a $C_1-C_2$ alkyl; and
each A is independently selected from $R^1$, $R^2$, $R^3$, and $R^4$, where
$R^1$ is:

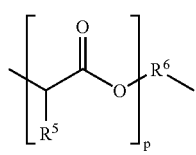

where:
p is an integer of 1 to 20;
$R^5$ is hydrogen or $C_1-C_4$ alkyl; and
$R^6$ is:

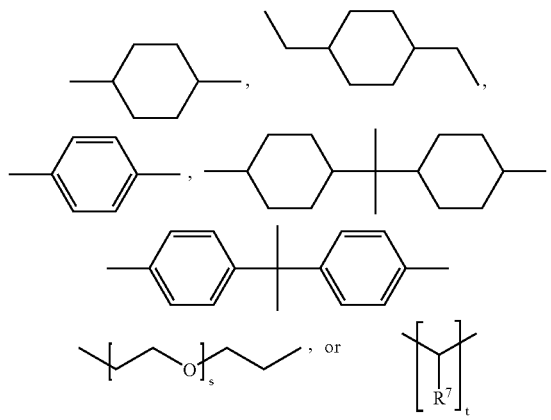

where:
s is an integer of 0 to 30;
t is an integer of 2 to 200; and
$R^7$ is hydrogen or $C_1-C_4$ alkyl;
$R^2$ is:

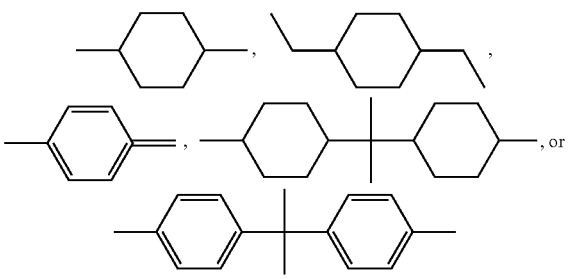

$R^3$ is:

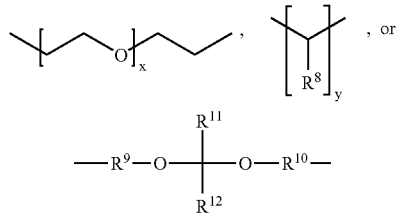

where:
x is an integer of 0 to 30;
y is an integer of 2 to 200;
$R^8$ is hydrogen or $C_1-C_4$ alkyl;
$R^9$ and $R^{10}$ are independently $C_1-C_{12}$ alkylene;
$R^{11}$ is hydrogen or $C_1-C_6$ alkyl and $R^{12}$ is $C_1-C_6$ alkyl; or
$R^{11}$ and $R^{12}$ together are $C_3-C_{10}$ alkylene; and
$R^4$ is (i) the residue of a diol containing at least one amine functionality incorporated therein, or (ii) the residue of a diol containing at least one functional group independently selected from amide, imide, urea, and urethane groups.

In a second aspect, this invention is controlled release pharmaceutical compositions comprising:

(a) an active agent; and (b) as a vehicle, the poly(ortho ester) described above.

In a third aspect, this invention is a method of treating a disease state treatable by controlled release local administration of an active agent, such as treating pain by administration of a local anesthetic or treating cancer by administration of a chemotherapeutic or antineoplastic agent, comprising locally administering a therapeutically effective amount of the active agent in the form of the controlled release pharmaceutical composition described above.

In a fourth aspect, this invention is methods of preparation of the poly(ortho esters) of the first aspect of the invention and the controlled release pharmaceutical compositions of the second aspect of the invention.

In a fifth aspect, this invention is block copolymers of formula X formula Y, and formula Z:

  (X),

  (Y),

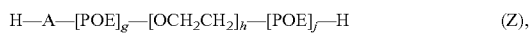  (Z), where:

$R^A$ is $C_1$–$C_4$ alkyl;

$R^B$ is $C_1$–$C_4$ alkyl;

f and h are independently an integer from 2 to 1000;

g and j are independently an integer from 2 to 200;

POE is a poly(ortho ester) unit of formula II:

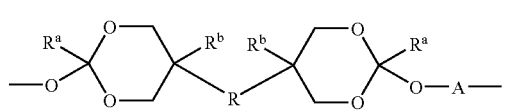

(II)

where

R is a bond, —$(CH_2)_a$—, or —$(CH_2)_b$—O—$(CH_2)_c$—; where a is an integer of 1 to 10, and b and c are independently integers of 1 to 5; and $R^a$ is a $C_1$–$C_4$ alkyl;

$R^b$ is hydrogen or a $C_1$–$C_2$ alkyl;

each A is independently selected from $R^1$, $R^2$, $R^3$, and $R^4$, where $R^1$ is:

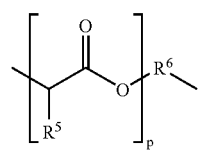

where:

p is an integer of 1 to 20;

$R^5$ is hydrogen or $C_1$–$C_4$ alkyl; and $R^6$ is:

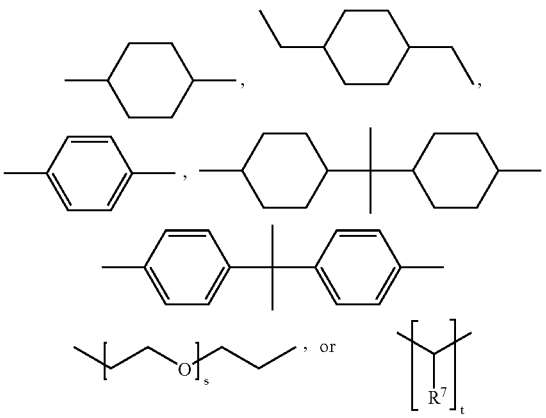

where:

s is an integer of 0 to 30;

t is an integer of 2 to 200; and $R^7$ is hydrogen or $C_1$–$C_4$ alkyl;

$R^2$ is:

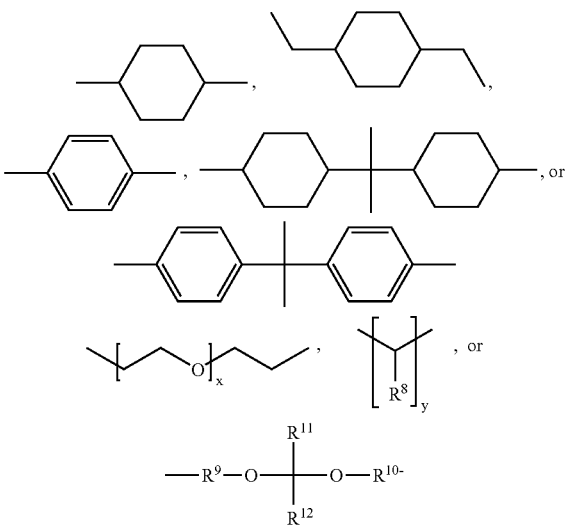

$R^3$ is:

where:

x is an integer of 0 to 30;

y is an integer of 2 to 200;

$R^8$ is hydrogen or $C_1$–$C_4$ alkyl;

$R^9$ and $R^{10}$ are independently $C_1$–$C_{12}$ alkylene;

$R^{11}$ is hydrogen or $C_1$–$C_6$ alkyl and $R^{12}$ is $C_1$–$C_6$ alkyl; or $R^{11}$ and $R^{12}$ together are $C_3$–$C_{10}$ alkylene; and $R^4$ is (i) the residue of a diol containing at least one amine functionality incorporated therein, or (ii) the residue of a diol containing at least one functional group independently selected from amide, imide, urea, and urethane groups.

In a sixth aspect, this invention is a micellar pharmaceutical composition for the delivery of a hydrophobic or water-insoluble active agent, comprising the active agent physically entrapped within but not covalently bonded to a drug carrier comprising a block copolymer of formula X, formula Y, or formula Z, or a mixture thereof.

In a seventh aspect, this invention is a composition for the sustained release of an active agent, comprising the active agent dispersed in a matrix comprising a block copolymer of formula X, formula Y, or formula Z, or a mixture thereof.

In an eighth aspect, this invention is a process for the preparation of a block copolymer of formula X, formula Y, or formula Z, as described in the "Detailed description of the invention".

DETAILED DESCRIPTION OF THE INVENTION

Definitions

Unless defined otherwise in this specification, all technical and scientific terms are used herein according to their conventional definitions as they are commonly used and understood by those of ordinary skill in the art of synthetic and pharmaceutical chemistry.

"Active agent" includes any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents. Suitable pharmaceutical agents include locally or systemically acting pharmaceutically active agents which may be administered to a subject by topical or intralesional application (including, for example, applying to abraded skin, lacerations, puncture wounds, etc., as well as into surgical incisions) or by injection, such as subcutaneous, intradermal, intramuscular, intraocular, or intra-articular injection. Examples of these agents include, but not limited to, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids, and the like), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors, and the like), cancer chemotherapeutic agents (e.g., mechlorethamine, cyclophosphanude, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen, and the like), narcotics (e.g., morphine, meperidine, codeine, and the like), local anesthetics (e.g., the amide- or anilide-type local anesthetics such as bupivacaine, dibucaine, mepivacaine, procaine, lidocaine, tetracaine, and the like), antiangiogenic agents (e.g., combrestatin, contortrostatin, anti-VEGF, and the like), polysaccharides, vaccines, antigens, DNA and other polynucleotides, antisense oligonucleotides, and the like. The present invention may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agents" further includes biocides such as fungicides, pesticides, and herbicides, plant growth promoters or inhibitors, preservatives, disinfectants, air purifiers and nutrients.

"Alkyl" denotes a linear saturated hydrocarbyl having from one to the number of carbon atoms designated, or a branched or cyclic saturated hydrocarbyl having from three to the number of carbon atoms designated (e.g., $C_1$–$C_4$ alkyl). Examples of alkyl include methyl ethyl n-propyl, isopropyl cyclopropyl, n-butyl, t-butyl, cyclopropylmethyl and the like.

"Alkylene" denotes a branched or unbranched saturated divalent radical having from one to the number of carbon atoms designated (e.g., $C_1$–$C_{12}$ alkylene). Examples of alkylene include methylene (—$CH_2$—), ethylene (—$CH_2CH_2$—), isopentylene (—$CH_2$—$CH(CH_3)$—$CH_2$—$CH_2$—), n-octylene (—$(CH_2)_8$—) and the like.

"Bioerodible" and "bioerodibility" refer to the degradation, disassembly or digestion of the poly(ortho ester) by action of a biological environment, including the action of living organisms and most notably at physiological pH and temperature. A principal mechanism for bioerosion of the poly(ortho esters) of the present invention is hydrolysis of linkages between and within the units of the poly(ortho ester).

"Comprising" is an inclusive term interpreted to mean containing, embracing, covering or including the elements listed following the term, but not excluding other unrecited elements.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the poly(ortho ester). The rate of hydrolysis in turn may be controlled by the composition of the poly(ortho ester) and the number of hydrolysable bonds in the poly(ortho ester). Other factors determining the rate of release of an active agent from the present pharmaceutical composition include particle size, acidity of the medium (either internal or external to the matrix) and physical and chemical properties of the active agent in the matrix.

"Matrix" denotes the physical structure of the poly(ortho ester) or block copolymer which essentially retains the active agent in a manner preventing release of the agent until the poly(ortho ester) or block copolymer erodes or decomposes.

"PEG" means polyethylene glycol, H—$[OCH_2CH_2]_k$—OH, with a numerical suffix indicating the nominal number average molecular weight, $M_n$. Unless the context requires otherwise, "PEG" also includes polyethylene glycol mono ($C_1$–$C_4$ alkyl) ethers, R—$[OCH_2CH_2]_k$—OH, where R is $C_1$–$C_4$ alkyl, sometimes referred to as "RPEG".

"POE" means a poly(ortho ester); or, in the case of the block copolymers, a poly(ortho ester) unit.

"Sequestration" is the confinement or retention of an active agent within the internal spaces of a poly(ortho ester) or block copolymer matrix. Sequestration of an active agent within the matrix may limit the toxic effect of the agent, prolong the time of action of the agent in a controlled manner, permit the release of the agent in a precisely defined location in an organism, or protect unstable agents against the action of the environment.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A "unit" denotes an individual segment of a poly(ortho ester) chain, which consists of the residue of a di(ketene acetal) molecule and the residue of a polyol.

An "α-hydroxy acid containing" unit denotes a unit where A is $R^1$, i.e. in which the diol is prepared from an α-hydroxy acid or cyclic diester thereof and a diol of the formula HO—$R^6$—OH. The fraction of the poly(ortho ester) that is α-hydroxy acid containing units affects the rate of hydrolysis (or bioerodibility) of the poly(ortho ester) or block copolymer containing it, and in turn, the release rate of the active agent.

An "amine containing" unit denotes a unit where the diol contains at least one amine functionality incorporated therein, which is one of the two types of units where A is $R^4$. The fraction of the poly(ortho ester) that is amine containing units affects the pH-sensitivity of the rate of hydrolysis (or bioerodibility) of the poly(ortho ester) or block copolymer containing it, and in turn, the release rate of the active agent.

"Hard" and "soft" units denote individual units of the poly(ortho ester), the fractions of which relative to the poly(ortho ester) as a whole determine the mechano-physical state of the poly(ortho ester) or block copolymer containing it. "Hard" units are units where A is $R^2$ and "soft" units are units where A is $R^3$.

A "hydrogen bonding" unit denotes a unit where the diol contains at least one functional group independently selected from amide, imide, urea, and urethane groups, which is one of the two types of units where A is $R^4$. The fraction of the poly(ortho ester) that is hydrogen bonding units determines the mechano-physical state of the poly(ortho ester) or block copolymer containing it.

"Vehicle" and "carrier" denote an ingredient that is included in a composition such as a pharmaceutical or cosmetic preparation for reasons other than a therapeutic or other biological effect. Functions served by vehicles and carriers include transporting an active agent to a site of interest, controlling the rate of access to, or release of, the active agent by sequestration or other means, and facilitating the application of the agent to the region where its activity is needed. Examples of vehicles and carriers include solids such as microparticles, microspheres, rods, and wafers; and semisolids that are dispensable by syringe or the like, or by spreading with a tool such as a spatula.

Ranges given, such as temperatures, times, sizes, and the like, should be considered approximate, unless specifically stated.

The poly(ortho esters)

The poly(ortho esters) are of formula I:

$$\left[ \begin{array}{c} R^a \\ \diagup \\ O \end{array} \begin{array}{c} O \\ \diagdown \\ O \end{array} \begin{array}{c} R^b \\ \diagup \\ R \end{array} \begin{array}{c} R^b \\ \diagdown \\ O \end{array} \begin{array}{c} O \\ \diagup \\ O \end{array} \begin{array}{c} R^a \\ \diagdown \\ O \end{array} A \right]_n \quad (I)$$

where n is an integer of at least 5;

R is a bond, —$(CH_2)_a$—, or —$(CH_2)_b$—O—$(CH_2)_c$—; where a is an integer of 1 to 10, and b and c are independently integers of 1 to 5;

$R^a$ is a $C_1$–$C_4$ alkyl;

$R^b$ is hydrogen or a $C_1$–$C_2$ alkyl; and each A is independently selected from $R^1$, $R^2$, $R^3$, and $R^4$, where $R^1$ is:

$$\left[ \begin{array}{c} O \\ \parallel \\ -C-CH-O-R^6-O- \\ | \\ R^5 \end{array} \right]_p$$

where:

p is an integer of 1 to 20;

$R^5$ is hydrogen or $C_1$–$C_4$ alkyl; and $R^6$ is:

[structures shown]

where:

s is an integer of 0 to 30;

t is an integer of 2 to 200; and $R^7$ is hydrogen or $C_1$–$C_4$ alkyl;

$R^2$ is:

[structures shown]

$R^3$ is:

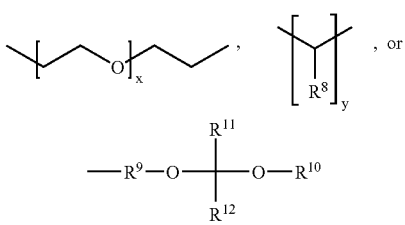

where:
x is an integer of 0 to 30;
y is an integer of 2 to 200;
$R^8$ is hydrogen or $C_1$–$C_4$ alkyl;
$R^9$ and $R^{10}$ are independently $C_1$–$C_{12}$ alkylene; $R^{11}$ is hydrogen or $C_1$–$C_6$ alkyl and $R^{12}$ is $C_1$–$C_6$ alkyl; or $R^{11}$ and $R^{12}$ together are $C_3$–$C_{10}$ alkylene; and
$R^4$ is (i) the residue of a diol containing at least one amine functionality incorporated therein, or
(ii) the residue of a diol containing at least one functional group independently selected from amide, imide, urea, and urethane groups.

Because these poly(ortho esters) are polymers, the number of repeating units n in the poly(ortho ester) necessarily represents the average value of a distribution rather than an exact number. Similarly, the number of α-hydroxy acid groups p in the α-hydroxy acid containing units and the number of ethylene oxide groups s and x in the $R^6$ and $R^3$ groups also necessarily represent the average values of distributions rather than exact numbers.

The structure of the poly(ortho ester) useful for the present invention, as shown in formula I, is one of alternating residues of a di(ketene acetal) and a diol, with each adjacent pair of di(ketene acetal) residues being separated by the residue of one polyol, preferably a diol. The poly(ortho esters) of the present invention are prepared by condensation reactions between diketene acetals) and polyols, preferably diols, and the variation in mechano-physical state and rate of hydrolysis (bioerodibility) is achieved by the selection and use of combinations of different types of diols.

The poly(ortho esters) can be prepared in such a manner that the rate and degree to which they are hydrolyzed by contact with bodily fluids at normal body temperature and pH can be controlled without addition of exogenous acid, by the incorporation of esters of short-chain α-hydroxy acids such as esters of glycolic acid, lactic acid or glycolic-co-lactic acid copolymer into the poly(ortho ester) chain and variation of the amount of these esters relative to the poly(ortho ester) as a whole.

In the presence of water, these esters, when incorporated into the poly(ortho ester) chain, are readily hydrolyzed at a body temperature of 37° C. and a physiological pH, in particular at a pH of 7.4, to produce the corresponding α-hydroxy acids. The α-hydroxy acids then act as an acidic excipient to control the hydrolysis rate of the poly(ortho ester). When the poly(ortho ester) is used as a vehicle or matrix entrapping an active agent, the hydrolysis of the poly(ortho ester) causes release of the active agent.

Poly(ortho esters) having a higher mole percentage of the "α-hydroxy acid containing" units will have a higher rate of bioerodibility. Preferred poly(ortho esters) for increased degradation rate are those in which the mole percentage of the "α-hydroxy acid containing" units is at least 0.1 mol %, e.g. about 0.1–99 mol %, such as about 0.5–50 mol %, more preferably about 1–30 mol %, for example about 5–30 mol %, especially about 10–30 mol %.

The use in these poly(ortho esters) of diols containing amine functionalities causes the poly(ortho esters) to become more pH-sensitive than poly(ortho esters) not containing such diols, and thus to hydrolyze yet more readily at lower pH than at higher pH. This is particularly so in an acidic aqueous environment, such as is found within animal cells, and enables the poly(ortho esters) to be relatively stable within the extracellular environment within an animal, such as within the blood, but to hydrolyze rapidly within the intracellular environment. This makes these poly (ortho esters) particularly suitable for delivery of active agents within the cell.

Poly(ortho esters) having a higher mole percentage of the "amine containing" units will have a rate of bioerodibility that is more pH-sensitive than non-"amine containing" poly (ortho esters), and increases at lower pH. Preferred poly (ortho esters) for a greater pH-sensitivity are those in which the mole percentage of the "amine containing" units is in the range of about 0.1–99.9 mol %, more preferably about 1–80 mol %, for example about 5–50 mol %, especially about 10–30 mol %.

In addition, the mechano-physical state of the poly(ortho ester) may also be controlled. This is achieved by the inclusion of the residues of certain diols in selected proportions relative to the poly(ortho ester) as a whole. For example, a high content of the residue of 1,4-cyclohexanedimethanol (as the trans isomer or as a cis/trans isomer mixture) or a similar "hard" diol or a "hydrogen bonding" diol relative to a "soft" diol (a definition of which is given below) produces a relatively rigid polymer chain and a more solid substance, and by decreasing the "hard" and "hydrogen bonding" diol content relative to the "soft" diol, the poly (ortho ester) will change progressively through the stages of a rigid thermoplastic, a soft thermoplastic, a low melting solid to an ointment-like (viscous liquid) material, and any stage in between.

Expressed in terms of mole percent of the "hard" or "hydrogen bonding" unit relative to the poly(orthoester) as a whole, preferred poly(ortho esters) for liquid or ointment-like compositions are those in which the "hard" or "hydrogen bonding" unit constitutes 20 mol % or less. Likewise, preferred poly(ortho esters) for more solid compositions are those in which the "hard" or "hydrogen bonding" unit constitutes 60 mol % or more.

Thus, both characteristics of the resulting poly(ortho ester) prepared from the reaction between the di(ketene acetal) of Formula III and a mixture of the diols, are controlled by the ratio of quantities of the two to four types of diols in the diol mixture.

With respect to the individual "α-hydroxy acid containing" unit, p is preferably 1 to 6, more preferably 1 to 4, most preferably 1 or 2, especially 1; $R^5$ is preferably hydrogen or methyl, especially hydrogen; $R^6$ is preferably:

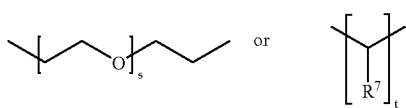

and in the above definitions of $R^6$, s is preferably 2 to 12, more preferably 2 to 6 and most preferably 2; $R^7$ is preferably hydrogen, and t is preferably 4 to 12, more preferably 4 to 6 and most preferably 6.

With respect to the individual "hard" unit, $R^2$ is preferably cyclohexanedimethanol.

With respect to the individual "soft" unit, $R^3$ is preferably:

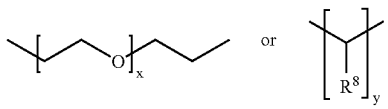

where x is preferably 2 to 12, more preferably 2 to 6 and most preferably 2; $R^8$ is preferably hydrogen, y is preferably 4 to 12, for example 10; otherwise, $R^9$ and $R^{10}$ are preferably identical, more preferably an unbranched $C_4$–$C_{12}$ alkylene, and especially an unbranched $C_6$–$C_{12}$ alkylene, $R^{11}$ is preferably hydrogen, and $R^{12}$ is preferably methyl.

With respect to the individual "amine containing" unit, diols of the formula HO—$R^4$—OH include aliphatic diols of 2 to 20 carbon atoms, preferably 2 to 10 carbon atoms, interrupted by one or two amine groups, and di(hydroxy)- or bis(hydroxyalkyl)-cyclic amines, having from 4 to 20, preferably 4 to 10, carbon or nitrogen atoms between the hydroxy groups; and the amine groups are secondary or, preferably, tertiary, amine groups.

Preferred poly(ortho esters) are those where one or more of the following are true:

(1) n is an integer of 5 to 500, preferably 20 to 500, especially 30 to 300;
(2) R is —$CH_2OCH_2$—;
(3) $R^a$ is $C_2$–$C_4$ alkyl, especially ethyl; and
(4) $R^b$ is ethyl;

and the proportions of and preferences for the individual units are as above.

While the presence of any of these preferences results in a poly(ortho ester) that is more preferred than the same poly(ortho ester) in which the preference is not met, the preferences are generally independent, and poly(ortho esters) in which a greater number of preferences is met will generally result in a poly(ortho ester) that is more preferred than that in which a lesser number of preferences is met.

Preparation of the poly(ortho esters)

The poly(ortho esters) are prepared according to the methods described in U.S. Pat. Nos. 4,764,364, 4,855,132, and 5,968,543. Specifically, the poly(ortho esters) are prepared by the reaction of a di(ketene acetal) of formula III:

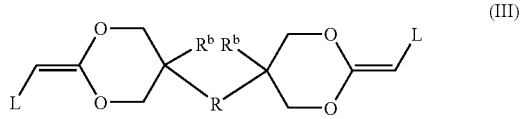

where L is hydrogen or a $C_1$–$C_3$ alkyl,
with a diol of the formula HO—$R^1$—OH, and optionally at least one diol of the formulae HO—$R^2$—OH, HO—$R^3$—OH, and HO—$R^4$—OH.

To form the poly(ortho ester) using a mixture of the various types of the diols, the mixture is formed with selected proportions based on the desired characteristics of the poly(ortho ester). The use of increasing amounts of diols in which A is $R^1$ increases the bioerodibility of the poly(ortho ester), and the use of such diols in which $R^6$ is a polyethyleneoxide moiety or an alkane increases the softness of the polymer; the use of increasing amounts of diols in which A is $R^2$ increases the hardness of the poly(ortho ester); and the use of diols in which A is $R^3$ increases the softness of the poly(ortho ester), especially when these diols are low molecular weight polyethylene glycols or aliphatic diols. The use of amine containing diols increases the pH-sensitivity of the bioerodibility of the poly(ortho ester), increasing it particularly at low pH, and the use of hydrogen bonding diols increases the hardness of the poly(ortho ester).

The preparation of di(ketene acetals) like those of formula III is disclosed in U.S. Pat. Nos. 4,304,767, 4,532,335, and 5,968,543; and will be known to a person of ordinary skill in the art. A typical method is the condensation of a bis(diol) of formula V:

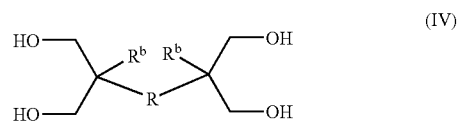

with two equivalents of a 2-halocarboxaldehyde dialkyl acetal such as 2-bromoacetaldehyde diethyl acetal followed by dehydrohalogenation to give the di(ketene acetal). The condensation of a glycol with diethylbromoacetals is described in Roberts et al., *J. Am. Chem. Soc.*, 80, 1247–1254 (1958), and dehydrohalogenation is described in Beyerstedt et al., *J. Am. Chem. Soc.*, 58, 529–553 (1936).

The di(ketene acetals) may also be prepared by the isomerization of di(vinyl acetals), prepared, for example, by the condensation of the bis(diol) of formula IV with two equivalents of a vinylic aldehyde, such as acrolein or crotonaldehyde, or their dialkyl acetals, such as acrolein dimethyl acetal, and such condensation reactions are well known. For example, Crivello et al., *J. Polymer Sci., Part A: Polymer Chemistry*, 34, 3091–3102 (1996), discloses the preparation of a number of ketene acetals and di(ketene acetals), including 2,2'-diethylidene-4,4'-bis-[1,3]dioxolane) and 3,9-diethylidene-2,4,8,10-tetraoxaspiro[5.5]undecane (DETOSU), in each case by the preparation of the corresponding di(vinyl acetal) from the relevant tetraol and acrolein and isomerization with tris(triphenylphosphine)-ruthenium dichloride.

The isomerization may be carried out by any of several methods known to the art. These include, in addition to the use of tris(triphenylphosphine)ruthenium dichloride mentioned immediately above, isomerization in alkali metal lower n-alkyl/water soluble primary amine solutions (U.S. Pat. No. 4,513,143) and in alkali metal alkoxide/ethyleneamine solutions (U.S. Pat. No. 4,532,335). A further isomerization method is photoisomerization in the presence of sensitizer such as a transition metal organometallic compound (e.g. iron pentacarbonyl) in an alkane (e.g. a pentane, hexane, or heptane) solvent under an inert atmosphere.

The bis(diol) of formula IV where R is a bond and each $R^b$ is hydrogen may be prepared by the reduction of the tetramethyl 1,1,2,2-ethanetetracarboxylate, available from Aldrich, with a reducing agent such as $LiAlH_4$ in a solvent such as diethyl ether, preferably at reduced temperature such as 0° C., to give the bis(diol). A reduction of this type is described in Haydock et al., *J. Med. Chem.*, 15:447–448 (1972) for the reduction of tetraethyl 1,1,4,4-butanetetracarboxylate.

The bis(diols) of formula IV where R is —(CH$_2$)$_a$— and each R$^b$ is hydrogen may be prepared by the reaction of an α,ω-dihaloalkane of the formula X—(CH$_2$)$_a$—X, where X is Cl or Br, such as 1,3-dibromopropane or 1,5-dibromopentane, with a dialkyl malonate of the formula CH$_2$(COOR$^3$)$_2$ where R$^3$ is C$_1$–C$_4$ alkyl, in the presence of a strong base such as an alkali metal or alkaline earth alkoxides (e.g. sodium or magnesium ethoxide) in a solvent such as a lower alkanoyl (e.g. ethanol) to give the tetraalkyl α,α,ω,ω-alkanetetracarboxylate. A coupling of this type is described in Meincke et al., *J. Amer. Chem. Soc.*, 57, 1133 (1935) for the preparation of tetraethyl 1,1,4,4-butanetetracarboxylate from diethyl malonate and 1,2-dibromoethane in the presence of magnesium ethoxide in ethanol. The thus-formed tetracarboxylate is then reduced to give the bis(diol). Other bis(diols) where each R$^b$ is non-hydrogen may be prepared from the corresponding dialkyl alkylmalonates, also available from Aldrich. The bis(diol) of formula IV where R is —CH$_2$— and each R$^b$ is hydrogen may also be prepared by the reaction of formaldehyde and a dialkyl malonate, such as diethyl malonate, as described by Haworth, *J. Chem. Soc.*, 73:330–345 (1898), followed by reduction of the thus-formed tetraethyl 1,1,3,3-propanetetracarboxylate to give the bis(diol).

The bis(diols) of formula IV where R is —(CH$_2$)$_b$—O—(CH$_2$)$_c$— may be prepared by a similar process, replacing the α,ω-dihaloalkane with a di(ω-haloalkyl) ether of the formula X—(CH$_2$)$_b$—O—(CH$_2$)$_c$—X, where X is Cl or Br.

The bis(diol) of formula IV where R is —CH$_2$—O—CH$_2$— and each R$^2$ is ethyl is di(trimethylolpropane) and is available from Aldrich and from Perstorp. Di(vinyl acetals) of formula II where R is —CH$_2$—O—CH$_2$— and each R$^2$ is H, methyl, or ethyl may also be prepared from the commercially available trimethylolmethane, trimethylolethane, and trimethylolpropane in the following manner:

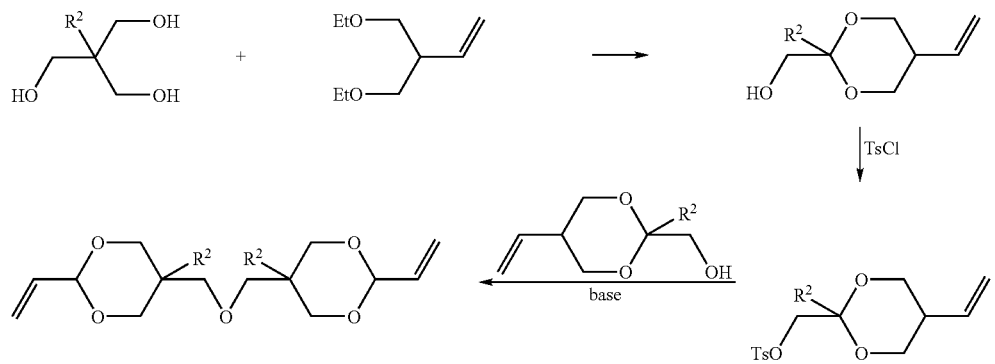

where the trimethylolalkane is first converted to the vinyl acetal by reaction with a vinylic aldehyde or its dialkyl acetal (acrolein diethyl acetal is shown), then some of the resulting alcohol converted to the a leaving group such as the tosylate (shown) or other alkane- or arenesulfonate, and that compound treated with base and the alcohol to form the di(vinyl acetal).

The rigidity or flexibility of the poly(ortho ester) is determined by the proportions of the "hard" units and "soft" units in the poly(ortho ester) structure, with greater rigidity achieved by including greater proportions of the "hard" units in the poly(ortho ester).

The diols of the formulae HO—R$^1$—OH, HO—R$^2$—OH, HO—R$^3$—OH, and HO—R$^4$—OH are prepared according to methods known in the art, and as described, for example, in U.S. Pat. Nos. 4,549,010 and 5,968,543. Some of the diols are commercially available.

The diol of the formula HO—R$^1$—OH may be prepared by reacting a diol of the formula HO—R$^6$—OH with 0.5–10 molar equivalents of a cyclic diester of an α-hydroxy acid, such as lactide or glycolide, and allowing the reaction to proceed at 100–200° C. for about 12–48 hours. Although particular solvents are not required for this reaction, organic solvents such as dimethylacetamide, dimethyl sulfoxide, dimethylformamide, acetonitrile, pyrrolidone, tetrahydrofuran, and methylbutyl ether may be used. Diols of the formula HO—R$^2$—OH are generally commercially available. Diols of the formula HO—R$^3$—OH may be commercially available or their preparation is generally disclosed in U.S. Pat. No. 5,968,543, by reacting an appropriate divinyl ether with an excess of an appropriate diol.

Amine containing diols of the formula HO—R$^4$—OH are diols containing at least one secondary or, preferably, tertiary amine. They include diols where R$^4$ is an amine such as R'NR''R''' or R'N=R''' where each of R' and R''' is independently an aliphatic, aromatic, or aromatic/aliphatic straight or branched chain hydrocarbyl to which is bonded one of the hydroxy groups of the diol, and optionally where R' and R''' are bonded so that the amine is a cyclic amine, especially a straight or branched chain alkyl of 2 to 10 carbon atoms, and more especially 2 to 5 carbon atoms, and R'' is hydrogen, C$_1$–C$_6$ alkyl, C$_6$–C$_{10}$ aryl, or aralkyl, especially alkyl, and more especially methyl. Other diols include those where two such amine groups are present, including in the same cyclic amine. Thus representative cyclic amine-based diols of the formula HO—R$^4$—OH include di(hydroxy)- or bis (hydroxyalkyl)-substituted cyclic amines such as substituted pyridine, pipetidine, pyridazine, pyrinidine, pyrazine, piperazine, and the like. Some representative diols of the formula HO—R$^4$—OH include N,N-bis(2-hydroxyethyl)amine, N,N-bis(2-hydroxyethyl)aniline, N-methyl-N,N-bis(2-hydroxyethyl)amine, N-butyl-N,N-bis(2-hydroxyethyl)amine, N-propyl-N,N-bis(2-hydroxyethyl)amine, N-2-propyl-N,N-bis(2-hydroxyethyl)amine, N-cyclohexyl-N,N-bis(2-hydroxyethyl)amine, N-benzyl-N,N-bis(2-hydroxyethyl)amine, 3-dimethylamino-1,2-propanediol, 3-(tert-butylamino)-1,2-propanediol, 1,4-bis(2-hydroxyethyl)piperidine, 1,4-bis(2-hydroxyethyl)piperazine, 1,4-bis (hydroxyethyl)piperazine, 7-(2,3-dihydroxypropyl)theophylline, 3,6-dihydroxypytidazine, 2,3-dihydroxypyridine, 2,4-dihydroxypyridine, 2,6-dihydroxypyridine, 4,6-dihydroxypyrimidine, N-ethyl-N,N-bis(2-hydroxyethyl)amine, and the like. Such diols include those containing both secondary and tertiary amines, though tertiary amines are preferred. Amine-containing polyols include N-3-hydroxypropyl-N,N-bis(2-hydroxyethyl)amine, 1,3-bis [tris(hydroxymethyl)methylamino]propane, 2,2-bis(hydroxymethyl)-2,2',2''-nitrilotriethanol, tris(2-hydroxyethyl)amine, tris(3-hydroxypropyl)amine, and the like. These diols are known to the art in reported syntheses and many are commercially available.

Hydrogen bonding diols include diols where $R^4$ is R'C(=O)NR''R' (amide), R'C(=O)NR''C(=O)R' (imide), R'NR''C(=O)NR''R' (urea), and R'OC(=O)NR''R' (urethane), where each R' is independently an aliphatic, aromatic, or aromatic/aliphatic straight or branched chain hydrocarbyl, especially a straight or branched chain alkyl of 2 to 22 carbon atoms, especially 2 to 10 carbon atoms, and more especially 2 to 5 carbon atoms, and R'' is hydrogen or $C_1$–$C_6$ alkyl, especially hydrogen or methyl, more especially hydrogen. Some representative diols of the formula HO—$R^4$—OH include N,N'-bis-(2-hydroxyethyl)terephthalamide, N,N'-bis-(2-hydroxyethyl)pyromellitic diimide, 1,1'-methylenedi(p-phenylene)bis-[3-(2-hydroxyethyl) urea], N,N'-bis-(2-hydroxyethyl)oxamide, 1,3-bis(2-hydroxyethyl)urea, 3-hydroxy-N-(2-hydroxyethyl)propionamide, 4-hydroxy-N-(3-hydroxypropyl)butyramide, and bis (2-hydroxyethyl)ethylenedicarbamate. These diols are known to the art in reported syntheses and many are commercially available. Representative diols of the formula HO—$(CH_2)_n$—NHCO—$(CH_2)_m$—OH where n is an integer of 2 to 6 and m is an integer of 2 to 5 are made by the reaction of 2-aminoethanol, 3-aminopropanol, 4-aminobutanol, 5-aminopentanol, or 6-aminohexanol with β-propiolactone, γ-butyrolactone, δ-valerolactone, or ε-caprolactone. Representative diols of the formula HO—$(CH_2)_n$—NHC(=O)O—$(CH_2)_m$—OH where n and m are each integers of 2 to 6 are made by the reaction of the same aminoalcohols just mentioned with cyclic carbonates of the formula:

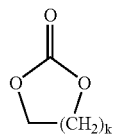

such as ethylene carbonate. Bis-amide diols of the formula HO—A—NHC(=O)—B—C(=O)NH—A—OH are prepared by the reaction of a diacid, optionally in activated form, such as the diacyldihalide, with two equivalents of a hydroxy-amine. Other methods of preparation of the diols of the formula HO—$R^4$—OH are known in the art.

Once made, the diol(s) of the formulae HO—$R^1$—OH, HO—$R^2$—OH, HO—$R^3$—OH, and HO—$R^4$—OH in the desired proportions are mixed with the di(ketene acetal) of formula III, in an approximately 1:1 ratio of total number of moles of di(ketene acetal) to total number of moles of diols, in a suitable solvent at ambient temperature. The condensation reaction between the di(ketene acetal) and the diols is carried out under conditions which are described in, for example, U.S. Pat. Nos. 4,764,364, 4,855,132, and 5,986,543, and are well known to those skilled in the art; and will also be readily apparent from the structures of the reactants themselves. Suitable solvents are aprotic solvents, such as dimethylacetamide, dimethyl sulfoxide, dimethylformamide, acetonitrile, acetone, ethyl acetate, pyrrolidone, tetrahydrofuran, and methylbutyl ether, and the like. Catalysts are not required for this reaction, but when used, suitable catalysts are iodine in pyridine, p-toluenesulfonic acid; salicylic acid, Lewis acids (such as boron trichloride, boron trifluoride, boron trichloride etherate, boron trifluoride etherate, stannic oxychloride, phosphorus oxychloride, zinc chloride, phosphorus pentachloride, antimony pentafluoride, stannous octoate, stannic chloride, diethyl zinc, and mixtures thereof); and Brønsted catalysts (such as polyphosphoric acid, crosslinked polystyrene sulfonic acid, acidic silica gel, and mixtures thereof). A typical amount of catalyst used is about 0.2% by weight relative to the di(ketene acetal). Smaller or larger amounts can also be used, such as 0.005% to about 2.0% by weight relative to the di(ketene acetal). Once the reaction is complete, the reaction mixture is allowed to cool and concentrated by rotoevaporation under vacuum, for a semi-solid poly(ortho ester); or by precipitation in a non-solvent such as an alkanol (e.g. methanol, ethanol and the like) or an alkane (e.g. hexanes, heptanes, and the like), for a solid poly(ortho ester). The poly(ortho ester) may be further dried under vacuum at an elevated temperature.

This invention also encompasses cross-linked poly(ortho esters) which are prepared by employing one or more polyols having more than two hydroxy functional groups. Such cross-linked poly(ortho esters) may be prepared preferably by first reacting the di(ketene acetal) with a diol in which A is $R^1$, $R^2$, $R^3$, $R^4$, or a mixture thereof, followed by addition of the polyol(s) having more than two hydroxy functional groups. Alternatively, the polyol(s) having more than two hydroxy functional groups may be added simultaneously with the diols. Polyols having more than two hydroxy functional groups suitable for the preparation of the cross-linked poly(ortho esters) may be the straight or branched chain type, including polyhydroxyl compounds such as 1,2,3-propanetriol, 1,2,5-pentanetriol, 1,2,6-hexanetriol, 1,3,5-pentanetriol, 1,2,4-butanetriol, 1,4,7-heptanetriol, 1,5,10-decanetriol, 1,5,12-dodecanetriol, 1,2,3,4,5,6-hexane-hexol, or such amine-containing polyhydroxyl compounds as tris(2-hydroxyethyl)amine and the like. Other representative polyols of the type are described in U.S. Pat. No. 4,304,767. The reaction conditions (e.g., suitable solvents and reaction temperatures) and procedures for the preparation of the cross-linked poly(ortho esters) are similar to those described above for the preparation of the poly (ortho esters) employing only the diols, and are also described in U.S. Pat. Nos. 4,304,767 and 5,968,543.

The poly(ortho esters) may also be prepared by reaction of the di(ketene acetal) with the chosen diols) under similar reaction conditions, but in the presence of a "chain stopper" (a reagent that terminates poly(ortho ester) chain formation. Suitable chain stoppers are $C_5$–$C_{20}$ alkanols, especially $C_{10}$–$C_{20}$ alkanols. The chain stopper is preferably present in from 1–20 mol % based on the di(ketene acetal). The poly(ortho esters) thus prepared have lower molecular weights with a lower molecular weight dispersion than those prepared by the reaction of the di(ketene acetals) with only diols.

The invention includes poly(ortho esters) which contain all types of units as well as poly(ortho esters) containing only one, two, three, or four types of units. It also includes poly(ortho esters) prepared from a mixture of units which contains two or more diols of the same type. It further includes poly(ortho esters) containing triols or higher polyols and/or "chain stopper" mono-alcohols, as described above.

The Block Copolymers

In a fifth aspect, this invention is block copolymers of formula X, formula Y, and formula Z:

 (X),

 (Y),

 (Z), where:
R$^A$ is C$_1$–C$_4$ alkyl;
R$^B$ is C$_1$–C$_4$ alkyl;
f and h are independently an integer from 2 to 1000;
g and j are independently an integer from 2 to 200;
POE is a poly(ortho ester) unit of formula II:

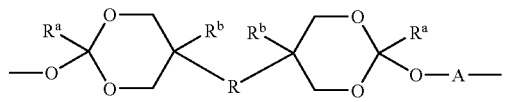 (II)

where
R is a bond, —(CH$_2$)$_a$—, or —(CH$_2$)$_b$—O—(CH$_2$)$_c$—; where a is an integer of 1 to 10, and b and c are independently integers of 1 to 5; and
R$^a$ is a C$_1$–C$_4$ alkyl;
R$^b$ is hydrogen or a C$_1$–C$_2$ alkyl;
each A is independently selected from R$^1$, R$^2$, R$^3$, and R$^4$, where
R$^1$ is:

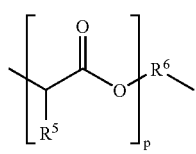

where:
p is an integer of 1 to 20;
R$^5$ is hydrogen or C$_1$–C$_4$ alkyl; and
R$^6$ is:

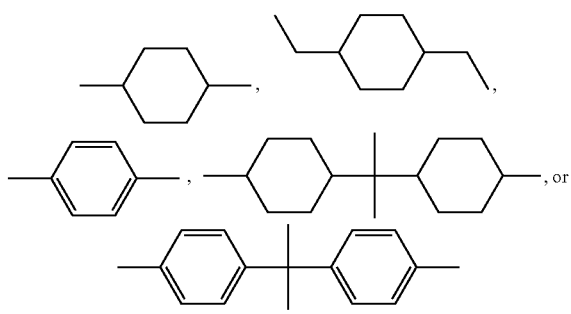

-continued

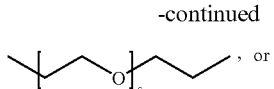

where:
s is an integer of 0 to 30;
t is an integer of 2 to 200; and
R$^7$ is hydrogen or C$_1$–C$_4$ alkyl;
R$^2$ is:

R$^3$ is:

where:
x is an integer of 0 to 30;
y is an integer of 2 to 200;
R$^8$ is hydrogen or C$_1$–C$_4$ alkyl;
R$^9$ and R$^{10}$ are independently C$_1$–C$_{12}$ alkylene;
R$^{11}$ is hydrogen or C$_1$–C$_6$ alkyl and R$^{12}$ is C$_1$–C$_6$ alkyl; or
R$^{11}$ and R$^{12}$ together are C$_3$–C$_{10}$ alkylene; and
R$^4$ is (i) the residue of a diol containing at least one amine functionality incorporated therein, or
(ii) the residue of a diol containing at least one functional group independently selected from amide, imide, urea, and urethane groups.

Because of the polymeric character of these molecules, the number of repeating units within the blocks, f, g, h, and j necessarily represent averages of distributions rather than exact numbers; and in particular, when f and h or g and j are described as being the same, this indicates that the average values of f and h, or of g and j, should be approximately the same. Similarly, the lengths of other polymeric chains, such as the poly(ethylene glycol) of R$^6$; of the long chain diol of R$^6$; and of the poly(α-hydroxy acid) group within R$^1$ necessarily represent averages of distributions rather than exact numbers.

The block copolymers are AB (formula X), ABA (formula Y), and BAB (formula Z) block copolymers in which the A blocks are hydrophilic poly(ethylene glycol) and the B blocks are hydrophobic poly(ortho ester). Within these, the poly(ortho ester) blocks are composed of alternating residues of a di(ketene acetal) and a diol.

The properties of the block copolymers, including both the mechanophysical properties and the bioerodibility, are determined by the type of the block copolymer, whether AB diblock, ABA triblock, or BAB triblock, the length of the PEG and POE blocks, and the diol(s) used in the POE blocks (in particular, the proportion of diol of the general formula HO—$R^1$—OH used in the POE blocks).

Preferred block copolymers are those in which one or more of the following are true:

(1) f and h are independently an integer from 10 to 500, especially from 50 to 250, for example 100, for micellar delivery; and f and h are independently an integer from 50 to 1000, especially from 100 to 1000, for example from 250 to 1000, for bioerodible matrices; and f and h are preferably the same if both are present;

(2) g and j are independently an integer from 5 to 100, especially 10 to 50, for example 15, for micellar delivery; and g and j are independently an integer from 10 to 200, especially from 20 to 200, for example from 50 to 200, for bioerodible matrices; and g and j are preferably the same if both are present;

(3) $R^A$ and $R^B$ are methyl;

(4) R is —$CH_2OCH_2$—;

(5) $R^a$ is $C_2$–$C_4$ alkyl, especially ethyl; and (6) $R^b$ is ethyl;

and the proportions of and preferences for the individual POE units are as above for the poly(ortho esters).

While a block copolymer having any one of these preferences listed above is preferred over a block copolymer not having that preference, the block copolymers will be more preferred the greater the number of preferences met.

Preparation of the Block Copolymers

The diblock copolymers of formula X are prepared in a two-step synthesis.

In the first step, a PEG lower alkyl ether of the formula $R^A$—[$OCH_2CH_2$]$_f$—OH, where $R^A$ is $C_1$–$C_4$ alkyl (an RPEG), is reacted with an excess of a di(ketene acetal) of formula III:

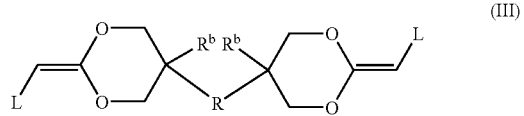

to form an intermediate of formula V:

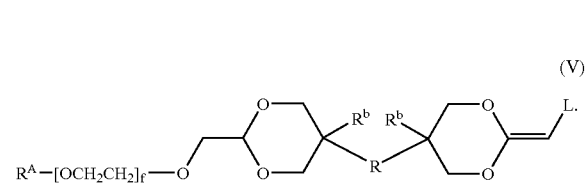

Polyethylene glycols, and polyethylene glycol lower alkyl ethers of various chain lengths (molecular weights) are available from a number of sources, including Aldrich Chemical Company, Inc., Milwaukee, Wis, and Shearwater Polymers, Huntsville, Ala.

In the second step, a diol of the formula HO—$R^1$—OH, HO—$R^2$—OH, HO—$R^3$—OH, or HO—$R^4$—OH, or a mixture thereof, is reacted with the solution of the first step (containing the intermediate of formula V and the excess di(ketene acetal)) to extend the POE block, thereby forming the diblock copolymer of formula X.

Since the di(ketene acetal) and the diol react in a 1:1 ratio to form the POE block of the diblock copolymer, the quantities of the RPEG, the di(ketene acetal), and the diol are chosen so that the molar amount of di(ketene acetal) is equal to the sum of the molar amounts of the RPEG and the diol.

The value of f in the PEG block, i.e. the length of the PEG block, is determined by the RPEG chosen. The value of g in the POE block, i.e. the length of the POE block, is determined by the molar quantity of diol relative to the molar quantity of RPEG: the greater the molar quantity of diol (assuming that the di(ketene acetal) is present in at least an equimolar quantity), the longer is the POE block.

The triblock copolymers of formula Y are also formed in a two-step synthesis.

In the first step, an excess of the di(ketene acetal) of formula III is reacted with a diol of the formula HO—$R^1$—OH, HO—$R^2$—OH, HO—$R^3$—OH, or HO—$R^4$—OH, or a mixture thereof, to form a POE block which is terminated at each end with a di(ketene acetal) unit, giving an intermediate of formula VI:

IV

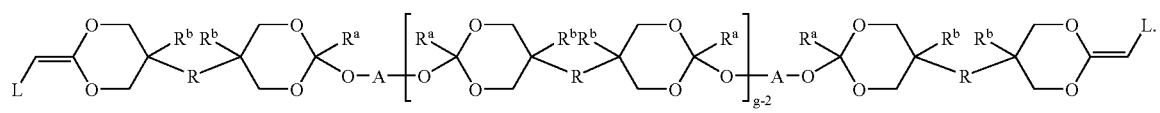

In the second step, the intermediate of formula VI is reacted with two equivalents of PEG or an RPEG to form the triblock copolymer of formula Y.

Since the di(ketene acetal) and the diol react in essentially a 1:1 ratio to form the POE block of the triblock copolymer, but di(ketene acetal) termination of the POE block is desired, the quantities of the di(ketene acetal) and the diol are chosen so that the molar amount of di(ketene acetal) is slightly greater than the molar amount of the diol. The molar ratio of PEG/RPEG to POE block should be approximately 2:1, but an excess of PEG/RPEG may be used, as it may be easily separated from the polymer after completion of the reaction.

The values of f and h for the PEG blocks are determined by the PEG/RPEG chosen. Typically f and h are the same, when a single PEG/RPEG is used; but if two or more PEGs/RPEGs of different lengths are used, then mixtures of copolymers containing varying PEG block lengths can be obtained, and these mixtures may be separated if desired, by such molecular weight fractionation techniques as gel permeation chromatography. The value of g for the POE block is determined primarily by the ratio of the di(ketene acetal) to the diol used to form the POE.

The triblock copolymers of formula Z are also formed in a two-step synthesis.

In the first step, a PEG of the formula H—[OCH$_2$CH$_2$]$_h$—OH is reacted with an excess of a di(ketene acetal) of formula III to form an intermediate of formula VII:

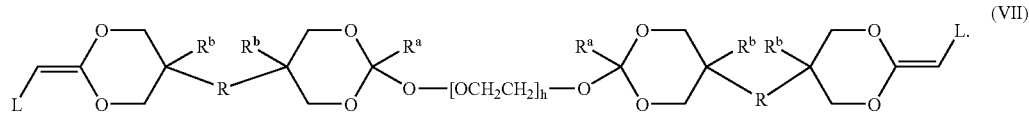

In the second step, a diol of the formula HO—R$^1$—OH, HO—R$^2$—OH, HO—R$^3$—OH, or HO—R$^4$—OH, or a mixture thereof, is reacted with the solution of the first step (containing the intermediate of formula VII and the excess di(ketene acetal)) to extend the POE blocks, thereby forming the triblock copolymer of formula Z.

Since the di(ketene acetal) and the diol react in a 1:1 ratio to form the POE blocks of the diblock copolymer, the quantities of the PEG, the di(ketene acetal), and the diol are chosen so that the molar amount of di(ketene acetal) is equal to the sum of the molar amounts of the PEG and the diol.

The value of h for the PEG block is determined by the PEG chosen. The values of g and j for the POE blocks are determined by the molar quantity of diol relative to the molar quantity of PEG: the greater the molar quantity of diol (assuming that the di(ketene acetal) is present in at least an equimolar quantity), the longer are the POE blocks. Typically the POE blocks will be of equal lengths, on average.

In an alternative synthesis of the triblock copolymer of formula Z, POE blocks terminated with di(ketene acetal) units (intermediates of formula V) are prepared, and reacted with 0.5 molar equivalent of PEG to terminate each end of the PEG with the POE blocks.

In any of the syntheses in which the copolymers may have an unreacted di(ketene acetal) terminal group, the copolymer may be reacted with a hydroxy-containing compound, such as a C$_1$–C$_4$ alcohol, to terminate the copolymer with alkoxy units; and such alkoxy-terminated copolymers are included within the scope of the invention. The hydroxy-containing compound, especially a C$_1$–C$_4$ alcohol, may be employed in excess and the unreacted excess easily separated during purification of the polymer.

Suitable reaction conditions for the formation of the copolymers are those conditions well known for the formation of poly(ortho esters), such as are described in U.S. Pat. No. 5,968,543 and the other documents cited in the "Background of the invention" section of this application. Typically, the reaction takes place in a polar aprotic solvent, such as those solvents mentioned previously for the preparation of the α-hydroxy acid containing diols, and ethers, especially tetrahydrofuran. A catalyst may be used if desired or necessary, and may be selected from those catalysts known to the art for the formation of orthoesters. Suitable such catalysts include iodine/pyridine, strong acids such as p-toluenesulfonic acid; Lewis acids, such as boron trichloride etherate, boron trifluoride etherate, tin oxychloride, phosphorus oxychloride, zinc chloride, phosphorus pentafluoride, antimony pentafluoride, stannic chloride, and the like; and Brønsted acids, such as polyphosphoric acid, polystyrenesulfonic acid, and the like. A particularly suitable catalyst is p-toluenesulfonic acid. A typical amount of catalyst used is about 0.2% by weight relative to the di(ketene acetal), though quantities between 0.005% and 2% may be used.

Suitable reaction temperatures are from room temperature to the boiling point of the solvent used, for example, between 20° C. and 70° C.; and suitable reaction times are between a few minutes and 48 hours, typically between 15 minutes and 24 hours.

Once the formation of the block copolymer is complete, the copolymer can be isolated by precipitation in a non-polar aprotic solvent such as hexane. Typically, the reaction mixture containing the copolymer (which may be cooled before the addition) is added slowly to about ten volumes of the rapidly stirred solvent at room temperature. The precipitated block copolymer may be collected by filtration, decantation, or other suitable method, washed to remove unreacted monomers or other contaminants, and dried, typically in a vacuum oven at a temperature below its melting point.

The bioerodibility of a block copolymer of this invention is determined by two factors: first, the extent to which the copolymer will dissolve/become suspended intact in an aqueous medium, the solubility of the copolymer; and second, the extent to which the copolymer, or, to be more precise, the POE block(s), will degrade in the environment to which it is exposed. The speed of degradation of the POE block(s) of the copolymer in an aqueous environment is determined by the hydrophilicity of the copolymer and by the proportion of α-hydroxy acid ester groups, if present, in the block(s), with greater bioerodibility being achieved particularly by inclusion of a greater proportion of diols of the formula HO—R$^1$—OH in the diol mixture used to form the POE block(s).

Uses of the poly(ortho esters)

The present poly(ortho esters) can be used for any use in which bioerodible polymers are usable, such as vehicles for the sustained release of an active agent.

To use the poly(ortho ester) as a sustained-release vehicle or carrier, the active agent must be incorporated into a matrix of the poly(ortho ester) or encapsulated within a capsule (or a "microcapsule" or "nanocapsule", as those terms are sometimes used) of the poly(ortho ester). Methods for the preparation of sustained-release dosage forms using biodegradable polymers are well known in the art, as discussed in the references cited in the "Description of the related art" section of this application, and in other references familiar to those of ordinary skill in the art; so that a person of ordinary skill in the art would have no difficulty, having regard to that skill and this disclosure, in preparing sustained-release formulations using the poly(ortho ester) of this invention. Suitable active agents include therapeutic agents such as pharmaceutical or pharmacological active agents, e.g. drugs and medicaments, as well as prophylactic agents, diagnostic agents, and other chemicals or materials useful in preventing or treating disease. The compositions of this invention are particularly useful for the therapeutic treatment of humans and other mammals, but may also be used for other animals. In addition, the sustained-release compositions of this invention may also be used for the release of cosmetic and agricultural agents, or for the release of biocides, such as fungicides or other pesticides, into an environment where prolonged release of the active agent is desired.

In the case of matrix formulations, the poly(ortho ester) is first mixed with the active agent. High homogeneity may be achieved by mixing the poly(ortho ester) in its heat softened state with the active agent, followed by lowering the temperature to harden the composition. Alternatively, the poly (ortho ester) can be dissolved in an appropriate casting solvent, such as tetrahydrofuran, methylene chloride, chloroform or ethyl acetate, and the active agent can then be dispersed or dissolved in the poly(ortho ester) solution, followed by evaporating the solvent to achieve the finished composition. Another method is grinding a solid poly(ortho ester) material into powder which is then mixed with a powdered active agent. The active agent may also be incorporated into the mixture of monomers before polymerization provided that it is stable under the polymerization conditions and does not interfere with the polymerization reaction.

If the active agent is one that is unstable at elevated temperatures (e.g. above 40° C.), or in the presence of organic solvents or organic solvent/water mixtures, such as a protein, then special preparation techniques may be required to minimize the exposure of the active agent to damaging conditions. Such techniques are disclosed in, for example, U.S. Pat. No. 620,697, which discloses ultrasonic melting to form matrix-type pharmaceutical compositions, and U.S. Pat. No. 5,518,730, which discloses melt-spinning, both of which techniques are designed to minimize the exposure of the polymer and active to elevated temperatures. Other methods are disclosed in the patents and literature references cited elsewhere in this application.

An alternate method for the incorporation and release of sensitive therapeutic agents is to use bioerodible poly(ortho esters) that have physical properties tailored for this incorporation. For example, the poly(ortho ester) may be chosen so that it is semi-solid and has an ointment-like consistency, rather than being fully solid. Thus, a poly(ortho ester) may be chosen that has a very high viscosity at normal body temperature of 37° C. so that little if any deformation takes place at that temperature. However, the viscosity of the poly(ortho ester) may decrease substantially at temperatures no higher than 45° C., or preferably by 40° C., so that injection of the material may be possible at a temperature at which the active agent retains its activity.

The composition obtained from any of the above methods can be readily processed into a variety of shapes and forms for implantation, insertion or placement on the body or into body cavities or passageways. For example, the poly(ortho ester) composition may be injection molded, extruded or compressed into a thin film or made into devices of various geometric shapes or forms such as flat, square, round, cylindrical tubular, disc, ring and the like. Rod- or pellet-shaped devices may be implanted through a trocar, such as is known for Norplant® implants, and these or other shapes may be implanted by minor surgical procedures. Alternatively, a device may be implanted following a major surgical procedure such as tumor removal in the surgical treatment of cancer. The implantation of polymer wafers containing anticancer agents is described, for example, in U.S. Pat. Nos. 5,626,862 and 5,651,986, and references cited therein; and the poly(ortho esters) of this invention will find utility in such applications.

The poly(ortho ester) composition may also be injected by syringe subcutaneously or intramuscularly as particles of 0.1–1000 μm, preferably 0.5–200 μm, and more preferably 1–150 μm suspended in a pharmaceutically acceptable injection base. Liquid vehicles useful for suspending the drug-poly(ortho ester) composition for injection include isotonic saline solution or oils (such as corn oil cottonseed oil, peanut oil and sesame oil) which, if desired, may contain other adjuvants.

Another injectable dosage form may be prepared from an active agent mixed in a poly(ortho ester) of the present invention which has an semi-solid consistency or which, when mixed with a suitable liquid excipient, forms a semi-solid composition such as the compositions described in U.S. patent application Ser. No. 09/854,180 (International Publication No. WO 01/85139). Such a dosage form may be administered by injection. Such a dosage form may also be administered by direct application to an area to be treated, such as by spreading into a wound with a spatula.

The poly(ortho ester) composition administered by either injection or implantation undergoes bioerosion in the body into non-toxic and non-reactive materials. By controlling the number of hydrolyzable bonds in the poly(ortho ester), the active agent may be released at a desired rate. Implants prepared from the present poly(ortho esters) in which the poly(ortho ester) constitutes the matrix containing an active agent also have the advantage that they do not require removal because of the bioerodibility of the poly(ortho ester).

In some cases, particles with cores of the pure active agent coated with various thicknesses of the present poly(ortho ester) may be preferred for sustained delivery of the active agent. Coating or encapsulation of discrete particles of the active agent may be accomplished by conventional methods which are all well-known to the person skilled in the art. For example, finely divided drug particles may be suspended in a solvent system (in which the drug is not soluble) containing the dissolved poly(ortho ester) and other excipients, followed by spray drying. Alternatively, the drug particles may be placed in a rotating pan or a fluid-bed dryer and the poly(ortho ester) dissolved in a carrier solvent is sprayed onto the drug particles until a suitable coating quantity is deposited on the particles to give a desired thickness. The coating may also be achieved by suspending the drug particles in a solvent system containing the dissolved poly (ortho ester) followed by adding to the suspension a non-solvent causing the poly(ortho ester) to precipitate and form a coating over the drug particles.

For the sustained release compositions, because the active agent will be released over a controlled period of time, the agent usually is present in an amount which is greater than the conventional single dose. The relative proportions of the active agent and the poly(ortho ester) can vary over a wide range (e.g., 0.1–50 wt. %) depending on the therapeutic agent and the desired effect.

Sustained compositions of cosmetic and agricultural agents may also be prepared by any one of the methods as described above, using the poly(ortho esters) of the present invention.

The solid poly(ortho esters) (those containing a high percentage of the "hard" unit and/or a high proportion of the "hydrogen bonding" unit) are also useful for a variety of orthopedic applications. For example, they can be used as fracture fixation devices for repair of osteochondral defects, ligament and tendon reconstructions and bone substitutes. In addition, the fact that the present poly(ortho esters) permit simultaneous selection of both a desired level of their mechano-physical state and a desired rate of bioerodibility, also renders them attractive as grafts or scaffolds on which cells can be cultured in vitro prior to implantation to regenerate tissues. Tissues which can be regenerated using this approach include but not limited to, bone, tendon, cartilage, ligaments, liver, intestine, ureter and skin tissues. For example, the poly(ortho esters) may be used to regenerate skin for patients with burns or skin ulcers. Cartilages may be repaired by first isolating chondrocytes from a patient (or a donor), allowing them to proliferate on the scaffolds prepared from the present poly(ortho ester) and re-implanting the cells in the patient.

The poly(ortho ester) scaffolds or implants may further contain other biologically active substances or synthetic inorganic materials such as reinforcing filler material for enhancing the mechanical properties of the scaffolds or implants (e.g. calcium sodium metaphosphate fibers), antibiotics or bone growth factors to induce and/or promote orthopedic restoration and tissue regeneration.

The compositions are also stable. The release rates of the active agent are not significantly affected by irradiation for sterilization.

Particular Compositions and Their Uses

Exemplary compositions of this invention, and their uses, include:

(1) compositions containing local anesthetics, optionally in combination with glucocorticosteroids such as dexamethasone, cortisone, hydrocortisone, prednisone, prednisolone, beclomethasone, betamethasone, flunisolide, fluocinolone acetonide, fluocinonide, triamcinolone, and the like, for the prolonged relief of local pain or a prolonged nerve blockade;

(2) compositions containing cancer chemotherapeutic agents, such as those listed above under "Active agents", for deposition by syringe or by injection into tumors or operative sites from which a tumor has been ablated, for tumor control or treatment and/or the suppression of regrowth of the tumor from residual tumor cells after ablation of the tumor;

(3) compositions containing progestogens, such as flurogestone, medroxyprogesterone, norgestrel, norgestimate, norethindrone, and the like, for estrus synchronization or contraception;

(4) compositions containing antimetabolites such as fluorouracil and the like, as an adjunct to glaucoma filtering surgery; compositions containing antiangiogenic agents such as combrestatin, contortrostatin, and anti-VEGF agents, for the treatment of macular degeneration and retinal angiogenesis; and other compositions for the controlled release of ophthalmic drugs to the eye;

(5) compositions containing therapeutic polypeptides (proteins), such as insulin, luteinizing hormone releasing factor antagonists, and the like, for the controlled delivery of these polypeptides, avoiding the need for daily or other frequent injection;

(6) compositions containing anti-inflammatory agents such as the NSAIDs, e.g., ibuprofen, naproxen, COX-1 or COX-2 inhibitors, and the like, or anti-inflammatory steroids, for deposition by injection into inflamed tissue or intra-articular injection;

(7) compositions containing antibiotics, for the prevention or treatment of infection, especially for deposition into surgical sites to suppress post-operative infection, or into or on wounds, for the suppression of infection (e.g. from foreign bodies in the wound);

(8) compositions containing morphogenic proteins such as bone morphogenic protein; and (9) compositions containing DNA or other polynucleotides, such as antisense oligonucleotides.

Uses of the Block Copolymers

While the block copolymers of this invention will find utility in any of the uses for which biodegradable polymers are useful, including such uses as vehicles for the sustained release of active agents, orthopedic implants, degradable sutures, and the like, they will also find particular utility in applications where their nature as block copolymers having both hydrophobic and hydrophilic blocks confers a special benefit, and these uses will be addressed in greater detail, since a person of ordinary skill in the art will be well acquainted with the uses of biodegradable polymers and will have no difficulty, having regard to the skill of the art and this disclosure, in adapting the block copolymers of this invention to such uses.

Micellar System for Targeting of Tissues with EPR (Tumors and Inflamed Tissues)

Polymers useful as micellar delivery systems can be prepared by forming diblock, AB, or triblock, ABA or BAB, copolymers comprising a hydrophilic polyethylene glycol) A block and a hydrophobic poly(ortho ester) B block.

When such block copolymers are placed in water, in which the poly(ethylene glycol) block is soluble and the poly(ortho ester) block is insoluble, the block copolymer chains will spontaneously self-aggregate to form micellar structures. The hydrodynamic diameter of such micelles, which may be determined by methods such as dynamic light scattering, will be in the order of 10–30 nm. As may be determined by methods such as static light scattering, such micelles will contain several hundred polymer chains. The micelles will undergo a secondary, reversible association, giving particles of an average diameter of about 100 nm. While such micelles are too large to be excreted by the kidneys, individual block copolymers are not. Further, since the poly(ortho ester) segments can be made to be biodegradable, facile renal excretion will take place.

The major utility of such micellar systems resides in their ability to entrap and solubilize hydrophobic drugs in the hydrophobic core. Such entrapment is easily carried out in a number of ways. Thus, the drug can be added to the aqueous solution containing micelles and incorporated by simple stirring, by heating to moderate temperatures, or by ultrasonication. The micelles are efficient carriers for a variety of hydrophobic or insoluble active agents, and are particularly suitable as carriers for anticancer agents, which will accumulate in the tumor by an endocytotic process.

Efficient entrapment of hydrophobic drugs requires a highly hydrophobic core. Using AB, ABA, or BAB block copolymers where the hydrophobic B block forms a biodegradable, highly hydrophobic poly(ortho ester) core will allow preparation of systems with significantly enhanced entrapment efficiency relative to other biodegradable segments such as poly(L-lactic-co-glycolic acid) copolymers.

While any of the anticancer agents that can form micellar complexes are suitable for this use, anticancer agents that are particularly suitable for micellar tumor targeting are those with low water solubility or high aromatic content, such as the anthracycline antibiotics (e.g. doxorubicin, daunorubicin, and epirubicin), mitomycin C, paclitaxel and its analogs (e.g. docetaxol), platinum analogs (e.g. cisplatin and carboplatin), and the like. Other agents may include anticancer proteins, such as neocarzinostatin, L-asparaginase, and the like, and photosensitizers used in photodynamic therapy. Similarly, while any of the anti-inflammatory agents that can form micellar complexes are suitable for this use, anti-inflammatory agents that are particularly suitable for micellar targeting are those with low water solubility or high aromatic content, such as the anti-inflammatory steroids (e.g., cortisone, hydrocortisone, dexamethasone, prednisone, prednisolone, beclomethasone, betamethasone, flunisolide, fluocinolone acetonide, fluocinonide, triamcinolone, and the like) and the non-ionized NSAIDs (e.g., naproxen, nabumetone, ketoprofen, mefenamic acid, fenbufen, piroxicam, meloxicam, celecoxib, rofecoxib, and the like).

Bioerodible Block Copolymer Matrix for Controlled Drug Delivery

In the block copolymers of this invention, phase separation will occur where domains of the B block form within the continuous A-phase or vice versa. Such phase-separated material will have unique and useful thermal properties. Specifically, unlike poly(ortho esters) containing short segments of PEG within the poly(ortho ester), which when heated will gradually soften, PEG/POE AB, ABA, or BAB block copolymers have relatively sharp melting points. Further, while poly(ortho esters) containing short segments of poly(ethylene glycol) that have low softening temperatures have very poor mechanical properties, the copolymers of this invention, even those having very low melting temperatures, will retain mechanical properties suitable for use as implants.

The copolymers may be used as a sustained-release vehicle in the same manner as described above for the poly(ortho esters).

The copolymer composition administered by either injection or implantation undergoes bioerosion in the body into non-toxic and non-reactive materials. By controlling the number of hydrolysable bonds in the polymer, the active agent may be released at a desired rate. Implants prepared from the present copolymers in which the copolymer constitutes the matrix containing an active agent also have the advantage that they do not require removal because of the bioerodibility of the copolymer.

Sustained compositions of cosmetic and agricultural agents may also be prepared by any one of the methods as described above, using the copolymers of the present invention.

The solid copolymers are also useful for a variety of orthopedic applications in the same way as described previously for the poly(ortho esters).

The compositions are also stable. The release rates of the active agent are not affected by irradiation for sterilization.

Delivery of Controlled-release Local Anesthetics by Injection

Local anesthetics induce a temporary nerve conduction block and provide pain relief which lasts from a few minutes to a few hours. They are frequently used to prevent pain in surgical procedures, dental manipulations or injuries.

The synthetic local anesthetics may be divided into two groups: the slightly soluble compounds and the soluble compounds. Conventionally, the soluble local anesthetics can be applied topically and by injection, and the slightly soluble local anesthetics are used only for surface application. The local anesthetics conventionally administered by injection can also be divided into two groups, esters and non-esters. The esters include (1) benzoic acid esters (piperocaine, meprylcaine and isobucaine); (2) p-aminobenzoic acid esters (procaine, tetracaine, butethamine, propoxycaine, chloroprocaine); (3) m-aminobenzoic acid esters (metabutethamine, primacaine); and (4) p-ethoxybenzoic acid esters (parethoxycaine). The non-esters are largely anilides (amides), and include bupivacaine, lidocaine, mepivacaine, pyrrocaine and prilocaine.

Many of the local anesthetics are conventionally used in the form of their acid addition salts, as this provides solubility in aqueous injection media. However, because the presence of the large amount of acid within such a local anesthetic acid addition salt will result in more rapid degradation of the poly(ortho esters) or block copolymers of this invention and release of the local anesthetic, it is generally desirable to use the local anesthetics in free base form, or with only a small proportion of the acid addition salt present (addition of small quantities of the acid addition salt may provide enhanced release if desired).

The semi-solid injectable form of a local anesthetic of the present invention is prepared by incorporating the local anesthetic into the delivery vehicle in a manner as described above. The concentration of the local anesthetic may vary from 1–60 wt. %, preferably 5–30 wt. %, e.g., about 10 wt. %. The semi-solid composition is then filled into a syringe with a 18–25 gauge needle, and injected into sites that are painful or to be subjected to surgical procedures. The semi-solid injectable composition of the present invention can be used for controlled delivery of both slightly soluble and soluble local anesthetics.

Because the duration of action of a local anesthetic is proportional to the time during which it is in actual contact with nervous tissues, the present injectable delivery system can maintain localization of the anesthetic at the nerve for an extended period of time which will greatly prolong the effect of the anesthetic.

A number of authors, including in U.S. Pat. No. 6,046,187 and related patents, have suggested that the co-administration of a glucocorticosteroid may prolong or otherwise enhance the effect of local anesthetics, especially controlled-release local anesthetics; and formulations containing a local anesthetic and a glucocorticosteroid, and their uses for controlled release local anesthesia, are within the scope of this invention.

EXAMPLES

The following Preparation and Examples illustrate the preparation of poly(ortho esters) and block copolymers of this invention.

Preparation 1: Preparation of di[(5-ethyl-2-ethylidene-[1,3]dioxan-5-yl)methyl] ether (a compound of formula III where R is —CH$_2$OCH$_2$— and R$^b$ is ethyl

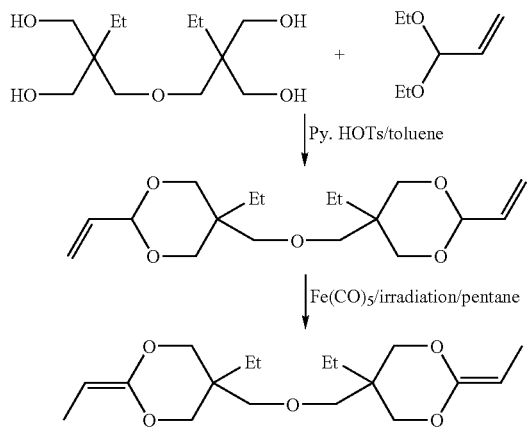

To 300 mL toluene in an 500 mL flask with condenser under a nitrogen atmosphere were added 30 g (120 mmol) di(trimethylolpropane), 45.6 mL (38.9 g, 300 mmol) acrolein diethyl acetal, and 1.5 g (6 mmol) pyridinium p-toluenesulfonate. The mixture was refluxed for 4 hours, then cooled to room temperature, and 0.67 g (6 mmol) potassium tert-butoxide added. The toluene was removed by evaporation under reduced pressure, and the residue distilled in a Kugelrohr apparatus (pressure 1–3 mbar, pot temperature 142–180° C.) to give 35.35 g (91% yield) of the two isomers of crude di[(5-ethyl-2-vinyl-[1,3]dioxan-5-yl)methyl] ether, as a light yellow oil. The crude product, 30 g, was purified by chromatography on 1 Kg Merck Silica Gel 60 in a 2 L glass fritted funnel, eluting with 20:80 ethyl acetate/heptane, to give 27.8 g (71% yield) of purer product, which was re-purified by a second chromatography on 1 Kg Merck Silica Gel 60 in a 2 L glass fritted funnel, eluting with 10:90 ethyl acetate/heptane, to give 16.44 g (42% yield) of essentially pure di[(5-ethyl-2-vinyl-[1,3]dioxan-5-yl)methyl] ether. This material was used in the photoisomerization.

To 220 mL pentane in a 500 mL photochemical reactor was added 14.32 g (43.9 mmol) di[(5-ethyl-2-vinyl-[1,3] dioxan-5-yl)methyl] ether from the previous step. The solution was refluxed vigorously for 20 minutes to degas it, then 115 μL (171 μg, 0.87 μmol, 0.2 mol %) iron pentacarbonyl was added, and the solution refluxed for an additional 20 minutes. The resulting solution was irradiated for one hour, by when NMR showed no vinyl signals. After cooling to room temperature and the addition of 0.5 mL triethylamine, the solution was sparged with dry air for 4 hours. The pentane was removed by evaporation under reduced pressure, and the residual oil was distilled in a Kugelrohr apparatus (pot temperature 220° C., pressure 1–3 mbar) to give 9.04 g (63% yield) of di[(5-ethyl-2-ethylidene-[1,3]-5-yl)methyl] ether as a colorless oil. The identity of the product was confirmed by $^1$H NMR and mass spectra (observed: 363, 345, calculated for C$_{18}$H$_{35}$O$_7$ (M+2H$_2$O+H$^+$): 363; calculated for C$_{18}$H$_{33}$O$_6$ (M+H$_2$O+H$^+$): 345).

Example 1

Preparation of poly(ortho esters) of Formula I

In a 100 mL round bottom flask was placed 1.143 g (3.5 mmol) di[(5-ethyl-2-ethylidene-[1,3]-dioxin-5-yl)methyl] ether (DEEDME), 0.743 g (4.95 mmol) triethylene glycol (TEG), 0.013 g (0.05 mmol) triethylene glycol monoglycolide (TEG-GL) and 5 mL tetrahydrofuran (THF). The reaction was initiated by the addition of a small amount of a salicylic acid solution in THF. After about 30 minutes, 0.1 mL triethylamine was added to neutralize the acidic catalyst and the solvent removed by evaporation to give a poly(ortho ester) of formula I where R is —CH$_2$OCH$_2$—, R$^a$ is ethyl, R$^b$ is ethyl, and A is a mixture of 1 mol % R$^1$ (where p is 1, R$^5$ is hydrogen, and R$^6$ is —CH$_2$CH$_2$OCH$_2$CH$_2$OCH$_2$CH$_2$—) and 99% R$^3$ (where R$^3$ is —CH$_2$CH$_2$OCH$_2$CH$_2$OCH$_2$CH$_2$—). [Need to fill in viscosity and MWt].

Following an identical procedure, 0.98 g (3.0 mmole) DEEDME, 0.743 g (4.95 mmol) TEG, and 0.013 g (0.05 mmol) TEG-GL were used to give a poly(ortho ester) of formula I where R is —CH$_2$OCH$_2$—, R$^a$ is ethyl, R$^b$ is ethyl, and A is a mixture of 1 mol % R$^1$ (where p is 1, R$^5$ is hydrogen, and R$^6$ is —CH$_2$CH$_2$OCH$_2$CH$_2$OCH$_2$ CH$_2$—) and 99% R$^3$ (where R$^3$ is —CH$_2$CH$_2$OCH$_2$CH$_2$OCH$_2$CH$_2$—). [Need to fill in viscosity and MWt].

Following an identical procedure, 1.469 g (4.5 mmol) DEEDME, 0.863 g (4.95 mmol) 1,10-decanediol, and 0.013 g (0.05 mmol) TEG-GL were used to give a poly(ortho ester) of formula I where R is —CH$_2$OCH$_2$—, R$^a$ is ethyl, R$^b$ is ethyl, and A is a mixture of 1 mol % R$^1$ (where p is 1, R$^5$ is hydrogen, and R$^6$ is —CH$_2$CH$_2$OCH$_2$CH$_2$OCH$_2$CH$_2$—) and 99% R$^3$ (where R$^3$ is —(CH$_2$)$_{10}$—). The molecular weight was 5,700 Da and the viscosity was 78,000 poise.

Following an identical procedure, 1.469 g (4.5 mmol) DEEDME, 0.743 g (4.95 mmol) TEG, and 0.013 g (0.05 mmol) TEG-GL were used to give a poly(ortho ester) of formula I where R is —CH$_2$OCH$_2$—, R$^a$ is ethyl, R$^b$ is ethyl, and A is a mixture of 1 mol % R$^1$ (where p is 1, R$^5$ is hydrogen, and R$^6$ is —CH$_2$CH$_2$OCH$_2$CH$_2$OCH$_2$ CH$_2$—) and 99% R$^3$ (where R$^3$ is —CH$_2$CH$_2$OCH$_2$CH$_2$OCH$_2$CH$_2$—). The molecular weight was 4,700 Da and the viscosity was 32,000 poise.

Other poly(ortho esters) of formula I are similarly prepared.

Example 2

Comparison of poly(ortho esters) Based on DEEDME and DETOSU

Following the procedure of Example 1, 1.632 g (5.0 mmol) DEEDME and 0.721 g (5.0 mmol) trans-cyclohexanedimethanol (CDM) were used to give a poly(ortho ester). The molecular weight was 11,400 Da and the glass transition temperature was 31.9° C. Using DETOSU instead of DEEDME gave a similar poly(ortho ester) having a glass transition temperature of 115° C. This illustrates the dramatic lowering in glass transition temperature of poly(ortho esters) achievable by using the flexible di(ketene acetals) of formula III.

Example 3

Preparation of a Diblock Copolymer of Formula X

Under anhydrous conditions, 2 g (1 mmol) PEG 2000 mono-methyl ether (MPEG 2000) and 3.26 g (10 mmol) DEEDME are weighed into a 50 mL flask and dissolved in 5 mL THF. A solution of p-toluenesulfonic acid in THF (5 µL, 20 mg/mL) is added to the MPEG 2000/DEEDME solution to initiate the reaction between the MPEG 2000 and the DEEDME, and the reaction mixture is stirred for about 20 minutes. CDM (1.32 g, 9.15 mmol) and 0.021 g (0.1 mmol) TEG-mGL in 5 mL THF are added to the flask, followed by another 5 µL p-toluenesulfonic acid solution. The reaction mixture is stirred for about 30 minutes, and then added dropwise to about 100 mL hexane with vigorous stirring, precipitating the diblock copolymer product, which is separated by filtration and dried in a vacuum oven.

Example 4

Preparation of a Triblock Copolymer of Formula Z

Under anhydrous conditions, 1.5 g (1.5 mmol) PEG 1000 and 3.26 g (10 mmol) DEEDME are weighed into a 50 mL flask and dissolved in 5 mL THF. A solution of p-toluenesulfonic acid in THF (5 µL, 20 mg/mL) is added to the PEG 1000/DEEDME solution to initiate the reaction between the PEG 1000 and the DEEDME, and the reaction mixture is stirred for about 20 minutes. CDM (1.15 g, 8 mmol) and 0.226 g (0.85 mmol) TEG-mGL in 5 mL THF are added to the flask, followed by another 5 µL p-toluenesulfonic acid solution. The reaction mixture is stirred for about 30 minutes, and then added dropwise to about 100 mL of hexane with vigorous stirring, precipitating the triblock copolymer product, which is separated by filtration and dried in a vacuum oven, giving a triblock POE-PEG-POE copolymer.

Other copolymers of formula X, Y, and Z are similarly prepared.

The foregoing is offered primarily for purposes of illustration. It will be readily apparent to those skilled in the art that the molecular structures, proportions of the reactant materials, methods of use and other parameters of the invention described herein may be further modified or substituted in various ways without departing from the spirit and scope of the invention.

What is claimed is:

1. A poly(ortho ester) of formula I:

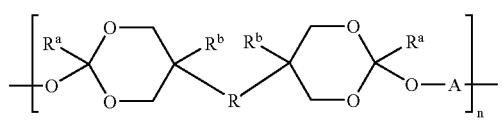

where
n is an integer of at least 5;
R is a bond, $-(CH_2)_a-$, or $-(CH_2)_b-O-(CH_2)_c-$, where a is an integer of 1 to 10, and b and c are independently integers of 1 to 5;
$R^a$ is a $C_1-C_4$ alkyl;
$R^b$ is hydrogen or a $C_1-C_2$ alkyl; and
each A is independently selected from $R^1$, $R^2$, $R^3$, and $R^4$, where
$R^1$ is:

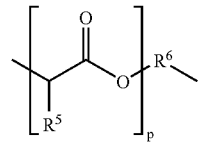

where:
p is an integer of 1 to 20;
$R^5$ is hydrogen or $C_1-C_4$ alkyl; and
$R^6$ is:

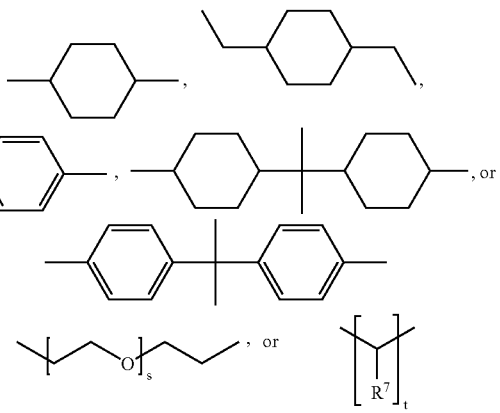

where:
s is an integer of 0 to 30;
t is an integer of 2 to 200; and
$R^7$ is hydrogen or $C_1-C_4$ alkyl;

$R^2$ is:

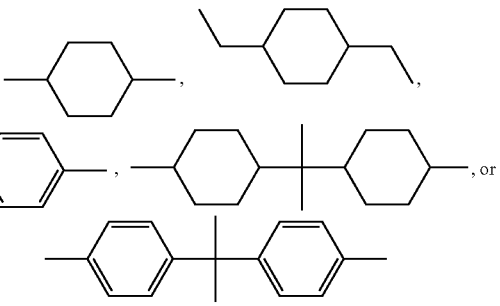

$R^3$ is:

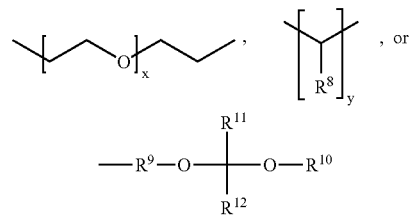

where:
- x is an integer of 0 to 30;
- y is an integer of 2 to 200;
- $R^8$ is hydrogen or $C_1$–$C_4$ alkyl;
- $R^9$ and $R^{10}$ are independently $C_1$–$C_{12}$ alkylene;
- $R^{11}$ is hydrogen or $C_1$–$C_6$ alkyl and $R^{12}$ is $C_1$–$C_6$ alkyl; or $R^{11}$ and $R^{12}$ together are $C_3$–$C_{10}$ alkylene; and
- $R^4$ is (i) the residue of a diol containing at least one amine functionality incorporated therein, or
  (ii) the residue of a diol containing at least one functional group independently selected from amide, imide, urea, and urethane groups.

2. The poly(ortho ester) of claim 1 where n is 5 to 500.

3. The poly(ortho ester) of claim 1 where R is —$CH_2OCH_2$—.

4. The poly(ortho ester) of claim 1 where $R^a$ is ethyl.

5. The poly(ortho ester) of claim 1 where $R^b$ is ethyl.

6. The poly(ortho ester) of claim 1 which comprises at least 0.1 mol % of units in which A is $R^1$.

7. The poly(ortho ester) of claim 6 which comprises about 0.5–50 mol % of units in which A is $R^1$.

8. The poly(ortho ester) of claim 7 which comprises about 1–30 mol % of units in which A is $R^1$.

9. The poly(ortho ester) of claim 1 where p is 1 to 2.

10. The poly(ortho ester) of claim 1 where $R^5$ hydrogen or methyl.

11. The poly(ortho ester) of claim 1 where $R^6$ is —$CH_2CH_2OCH_2CH_2OCH_2CH_2$—.

* * * * *